United States Patent
Nolan et al.

(10) Patent No.: US 7,179,598 B2
(45) Date of Patent: Feb. 20, 2007

(54) EARLY LEUKEMIA DIAGNOSTICS USING MICROSPHERE ARRAYS

(75) Inventors: John P. Nolan, Santa Fe, NM (US); Feng Zhou, Los Alamos, NM (US)

(73) Assignee: The Regents of the University of California, Oakland, CA (US)

( * ) Notice: Subject to any disclaimer, the term of this patent is extended or adjusted under 35 U.S.C. 154(b) by 419 days.

(21) Appl. No.: 10/301,300

(22) Filed: Nov. 20, 2002

(65) Prior Publication Data

US 2003/0198977 A1    Oct. 23, 2003

Related U.S. Application Data

(60) Provisional application No. 60/335,716, filed on Nov. 20, 2001.

(51) Int. Cl.
*C12Q 1/68* (2006.01)

(52) U.S. Cl. .......................... 435/6; 435/91.1

(58) Field of Classification Search .................. None
See application file for complete search history.

(56) References Cited

U.S. PATENT DOCUMENTS

| | | | |
|---|---|---|---|
| 5,633,135 | A | 5/1997 | Croce et al. |
| 6,203,992 | B1 | 3/2001 | Granados et al. |
| 6,287,766 | B1 * | 9/2001 | Nolan et al. ............ 435/6 |
| 6,355,431 | B1 | 3/2002 | Chee et al. |
| 6,428,957 | B1 | 8/2002 | Delenstarr |
| 2002/0025532 | A1 | 2/2002 | Huang et al. |

FOREIGN PATENT DOCUMENTS

WO  WO 98/24928  *  6/1998
WO  WO 98/24928 A2  6/1998

OTHER PUBLICATIONS

Cai et al. Genomics vol. 66:135-143. 2000.*
Cai, H. et al. "Flow cytometry-based minisequencing: a new platform for high-throughput single-nucleotide polymorphism scoring," *Genomics* 2000, pp. 135-143, vol. 66.
Fortina, P. et al. "Simple two-color array-based approach for mutation detection," *Eur. J. of Hum. Genet.* 2000, pp. 884-894, vol. 8.
Lieu, P. et al. "SureScore SNP genotyping kit: a single-base extension ELISA for discrimination of nucleotide polymorphisms," *Focus* 2002, pp. 6-9, vol. 24.
Look, T.A. "Oncogenic transcription factors in the human acute leukemias," *Science* Nov. 7, 1997, pp. 1059-1064, vol. 278.
Ma, S.K. et al. "Cytogenetics and molecular genetics of childhood leukemia," *Hematological Oncology* 1999, pp. 91-105, vol. 17.
Nolan, J.P. and Sklar, L.A. "Suspension array technology: evolution of the flat-array paradigm," *Trends in Biotechnol.* Jan. 1, 2002, pp. 9-12, vol. 20, No. 1.
Taylor, J.D. et al. "Flow cytometric platform for high-throughput single nucleotide polymorphism analysis," *BioTechniques* Mar. 2001, pp. 661-669, vol. 30.
Ye, F. et al. "Fluorescent microsphere-based readout technology for multiplexed human single nucleotide polymorphism analysis and bacterial identification," *Human Mutation* 2001, pp. 305-316, vol. 17.
Stratagene Catalog, Gene Characterization Kits, pp. 1-2 (1988).

* cited by examiner

*Primary Examiner*—Jeffrey Fredman
*Assistant Examiner*—Heather G Calamita
(74) *Attorney, Agent, or Firm*—Townsend & Townsend & Crew LLP

(57) ABSTRACT

The present invention provides methods and kits for detecting chromosome translocations. The present invention further provides methods for diagnosing cancer.

6 Claims, 17 Drawing Sheets

|  | frequency | |
|---|---|---|
|  | infants | others |
| e8-e7 | <10% | rare |
| e8-e4 | rare | <5% |
| e9-e5 | <10% | 16% |
| e9-e4 | rare | 25% |
| e10-e6 | rare | <5% |
| e10-e5 | <10% | <5% |
| e10-e4 | <18% | <39% |
| e11-e6 | Rare | <5% |
| e11-e5 | <10% | rare |
| e11-e4 | 55% | <5% |

FIG. 2

| Parent translocation | Oligo name | 5' position (strand) | Length (bp) | Sequence (5'-3') | |
|---|---|---|---|---|---|
| E2A-PBX1 | E2A-T | 1474 | 45(+) | CCAGGCACCCTCCCTGACCTGTCTCGGCCTCCCGACTCCTACAGT | SEQ ID NO:1 |
| | PBX1-T | 1563 | 45(+) | CCAGCTGATGCGGCTGGACAACATGCTGTTAGCGGAAGGCGTGGC | SEQ ID NO:2 |
| MLL-AF4 | AF4-T | 4021 | 45(+) | GATACATCTTCAAAAACTCACTCAAATTCTCAGCAAGGAACGTCA | SEQ ID NO:3 |
| | MLL-T | 3950 | 45(+) | AAGAAGTTCCAAAACCACTCCTAGTGAGCCAAGAAAAAGCAGC | SEQ ID NO:4 |
| AML1-ETO | AML1-T | 956 | 45(+) | AAAGCTTCACTCTGACCATCACTGTCTTCACAAACCCACCGAAG | SEQ ID NO:5 |
| | ETO-T | 1098 | 45(+) | GGATGTGAAGACGCAATCTAGGCTGACTCCTCAACAATGCCACC | SEQ ID NO:6 |
| BCR-ABL (p190) | BCR1-T | 1598 | 45(+) | CTCGCAGAACTCGCAACAGTCCTTCGACAGCAGTCCCCAC | SEQ ID NO:7 |
| BCR-ABL (p210) | ABL-T | 1776 | 45(+) | CTCCGGGTCTTAGGCTATAATCACAATGGGAATGGTGTGAAGCC | SEQ ID NO:8 |
| | BCR2-T | 3152 | 45(+) | ACTCCAGACTGTCCACAGCATTCCGCTGACCATCAATAAGGAAGA | SEQ ID NO:9 |
| TEL-AML1 | TEL-T | 958 | 45(+) | CTGGCTTACATGAACCACATCATGGTCTCTGTCTCCCGCCTGAA | SEQ ID NO:10 |
| | AML1-B-T | 1016 | 45(+) | CCATTGGGAGAATAGCAGATGCAGCAGAGCCGCGCGCTTCACGC | SEQ ID NO:11 |
| PML-RARA | PML-T | 1212 | 45(+) | GAGTTCAAGTGCGCCTGCAGGACCTCAGCTCTTGCATCACCCAG | SEQ ID NO:12 |
| | RARA-T | 1274 | 45(+) | CCAGAGCAGCAGTTCTGAAGAGATAGTGCCCAGCCCTCTCCGCC | SEQ ID NO:13 |
| CBFB-MYH11 | CBFB-T | 341 | 45(+) | GTATGGGCTGTGTCTGGAGTTTGATGAGGAGCGAGCCAGCAGGAGG | SEQ ID NO:14 |
| | MYH11-T | 501 | 45(+) | GGCCCTGAGACCCAGGAGATGGAGGAGATGAAGACGCAGCTGGAAGA | SEQ ID NO:15 |
| SIL-TAL1 | SIL-T | 81 | 45(+) | CTCCCGCTCCTACCCTGCAAACAGACCTCAGCTCCGCGGAAGTTG | SEQ ID NO:16 |
| | TAL1-T | 143 | 45(+) | GCCGAGCGAGGCGGCTCGCAGTGACCCCAGCTAGAGGGACGGGA | SEQ ID NO:17 |
| β-actin | Actin-T | 1003 | 45(+) | CACCCAGCACAATGAAGATCAAGATCATTGCTCCTCCTGAGCGCA | SEQ ID NO:18 |

*FIG. 7*

| Template | Primer name | 5' position (strand) | Length (bp) | Sequence (5'-3') | |
|---|---|---|---|---|---|
| E2A-PBX | E2A-F | 1434(+) | 19 | CACCAGCCTCATGCACAAC | SEQ ID NO:19 |
| | PBX-R | 1788(-) | 19 | TCGCAGGAGATTCATCACG | SEQ ID NO:20 |
| MLL-AF4 | MLL-F | 3916(+) | 17 | CCGCCTCAGCCACCTAC | SEQ ID NO:21 |
| | AF4-R | 4080(-) | 20 | TGTCACTGAGCTGAAGGTCG | SEQ ID NO:22 |
| AML1-ETO | AML1-A-F | 884(+) | 21 | CTACCGCAGCCATGAAGAACC | SEQ ID NO:23 |
| | ETO-R | 1258(-) | 21 | AGAGGAAGGCCCATTGCTGAA | SEQ ID NO:24 |
| BCR-ABL (p190) | BCR1-F | 1479(+) | 21 | GACTGCAGTCTCCAATGAGAAC | SEQ ID NO:25 |
| | ABL-R | 1805(-) | 21 | GTTTGGGCTTCACACCATTCC | SEQ ID NO:26 |
| BCR-ABL (p210) | BCR2-F | 3086(+) | 22 | GAAGTGTTTCAGAAGCTTCTCC | SEQ ID NO:27 |
| TEL-AML1 | TEL-F | 845(+) | 20 | TGCACCCTCTGATCCTGAAC | SEQ ID NO:28 |
| | AML1-B-R | 1085(-) | 19 | AACGCCTCGCTCATCTTGC | SEQ ID NO:29 |
| PML-RARA | PML-F | 969(+) | 18 | CTGCTGGAGGCTGTGGAC | SEQ ID NO:30 |
| | RARA-R | 1325(-) | 20 | GCTTGTAGATGCGGGGTAGA | SEQ ID NO:31 |
| CBFB-MYH11 | CBFB-F | 253(+) | 22 | GCAGGCAAGGTATATTTGAAGG | SEQ ID NO:32 |
| | MYH11-R | 649(-) | 22 | TCCTCTCTCCTCATTCTGCTC | SEQ ID NO:33 |
| SIL-TAL1 | SIL-F | 82(+) | 19 | TCCCGCTCCTACCCTGCAA | SEQ ID NO:34 |
| | TAL1-R | 279(-) | 18 | CGGGCCCAGTTCGATGAC | SEQ ID NO:35 |
| β-actin | Actin-F | 699(+) | 23 | GCCCTGGACTTCGAGCAAGAGAT | SEQ ID NO:36 |
| | Actin-R | 1361(-) | 23 | CCTCGGCCACATTGTGAACTTTG | SEQ ID NO:37 |

*FIG. 8*

| Template | Primer name | 5' position (strand) | Length (bp) | Sequence (5'-3') | |
|---|---|---|---|---|---|
| E2A-PBX1 | E2A-A | 1477 (-) | 40 | CGAGAGTTAGCTACAAAGCCGACAGGTCAGGAGGTGCC | SEQ ID NO:38 |
| | PBX1-B | 1581 (-) | 42 | CAGAACGCATTGTGAATAGGTGCCTTCCGCTAACAGCATGTTG | SEQ ID NO:39 |
| MLL-AF4 | MLL-A | 3968(-) | 44 | CACGGATGGATATATGAGCGCTTTTCTTGGGCTCACTAGGAG | SEQ ID NO:40 |
| | AF4-B | 4056(-) | 42 | GCACCTAGATAGGATCGTACCTCGAGCATGGATGACGTTCCT | SEQ ID NO:41 |
| AML1-ETO | AML1-A | 971(-) | 43 | GTCCAAGCTAGAGCGTTACGTGGGTTTGTGAAGACAGTGATGG | SEQ ID NO:42 |
| | ETO-B | 1114 (-) | 46 | GAATTGGGGCTACGAATAATGTCATTGTTGGAGGAGTCAGCCTAGA | SEQ ID NO:43 |
| BCR-ABL (p190) | BCR1-A | 1616(-) | 41 | TCGTCCGTAAAGATAATCGGGACTGCTGCTGTCGAAGGAC | SEQ ID NO:44 |
| | ABL-B | 1793(-) | 42 | TCTGTAGGAGGGCAAGAAACACACCATTCCCATTGTGATTA | SEQ ID NO:45 |
| BCR-ABL (p210) | BCR2-A | 3169(-) | 41 | CCTCCGCCATTTACCTAACTTATTGATGGTCAGCGGAATGC | SEQ ID NO:46 |
| | TEL-A | 975(-) | 42 | TGTCGCTAATTAGTTGGCTGCGGGAGACAGAGACCATGATG | SEQ ID NO:47 |
| TEL-AML1 | AML1-B | 1223(-) | 42 | CAGACTGAGATACTTCACTACGCAGCACGAGCAGAGAAGT | SEQ ID NO:48 |
| PML-RARA | PML-A | 1232(-) | 43 | GCGGCTCTATTTGAATTTCGGGTGATGCAAGAGCTGAGGTCC | SEQ ID NO:49 |
| | RARA-B | 1293(-) | 41 | CCTCCTTCCTTCATAAGCGTGGAGTGGGCTCGGGCACTATCTC | SEQ ID NO:50 |
| CBFB-MYH11 | CBFB-A | 357(-) | 39 | TGACTCGACTTTTGGGAGTGGGCTCGCTCCTCATCAAAC | SEQ ID NO:51 |
| | MYH11-B | 516(-) | 43 | AATTCGGACCCTAACATCTCGCTGCTCTTCATCTCCTCCATC | SEQ ID NO:52 |
| SIL-TAL1 | SIL-A | 93(-) | 40 | CGACAGCCGATAAACGAGGAGAGTCGAGGTCTGTTTGCAGGG | SEQ ID NO:53 |
| | TAL1-B | 163(-) | 39 | GGTCTCTTGATCAGGACGTCCCTCTAGCTGGGGTCAC | SEQ ID NO:54 |
| β-actin | Actin | 1018(-) | 44 | GGTATAGCCATGCGAGGTGTCAGGAGGAGCAATGATCTTGATCT | SEQ ID NO:55 |

FIG. 9

| Template | Primer name | 5' position (strand) | Length (bp) | Sequence (5'-3') | |
|---|---|---|---|---|---|
| E2A-PBX1 | E2A-A | 1477 (-) | 20 | GACAGGTCAGGGAGGGTGCC | SEQ ID NO:56 |
| | PBX1-B | 1581 (-) | 22 | GCCTTCCGCTAACAGCATGTTG | SEQ ID NO:57 |
| MLL-AF4 | MLL-A | 3968(-) | 24 | GCTTTTTCTTGGGCTCACTAGGAG | SEQ ID NO:58 |
| | AF4-B | 4056(-) | 21 | TCGAGCATGGATGACGTTCCT | SEQ ID NO:59 |
| AML1-ETO | AML1-A | 971(-) | 21 | GGTTTGTGAAGACAGTGATGG | SEQ ID NO:60 |
| | ETO-B | 1114 (-) | 24 | CATTGTTGGAGGAGTCAGCCTAGA | SEQ ID NO:61 |
| BCR-ABL (p190) | BCR1-A | 1616(-) | 21 | GGACTGCTGCTGTCGAAGGAC | SEQ ID NO:62 |
| BCR-ABL (p210) | ABL-B | 1793(-) | 23 | CACACCATTCCCATTGTGATTA | SEQ ID NO:63 |
| | BCR2-A | 3169(-) | 22 | TTATTGATGGTCAGCGGAATGC | SEQ ID NO:64 |
| TEL-AML1 | TEL-A | 975(-) | 22 | CGGGGAGACAGAGACCATGATG | SEQ ID NO:65 |
| | AML1-B | 1223(-) | 20 | CAGCACGGAGCAGAGGAAGT | SEQ ID NO:66 |
| PML-RARA | PML-A | 1232(-) | 22 | GGTGATGCAAGAGCTGAGGTCC | SEQ ID NO:67 |
| | RARA-B | 1293(-) | 21 | GGGAGGGCTGGGCACTATCTC | SEQ ID NO:68 |
| CBFB-MYH11 | CBFB-A | 357(-) | 21 | TGGGCTCGCTCCTCATCAAAC | SEQ ID NO:69 |
| | MYH11-B | 516(-) | 21 | GCTGCGTCTTCATCTCCTCCATC | SEQ ID NO:70 |
| SIL-TAL1 | SIL-A | 93(-) | 21 | GAGCTGAGGTCTGTTTGCAGGG | SEQ ID NO:71 |
| | TAL1-B | 163(-) | 21 | GTCCCTCTAGCTGGGGGTCAC | SEQ ID NO:72 |
| β-actin | Actin | 1018(-) | 25 | TCAGGAGGAGCAATGATCTTGATCT | SEQ ID NO:73 |

FIG. 10

| Samples | SBE primers | | | | | | | | | | | | | | | | | | | | | |
|---|---|---|---|---|---|---|---|---|---|---|---|---|---|---|---|---|---|---|---|---|---|---|
| | E2A-PBX1 | | AML1-ETO | | BCR1-ABL | | BCR2-ABL | | TEL-AML1 | | MLL-AF4 | | CBFB-MYH11 | | SIL-TAL1 | | PML-RARA | | RARA-actin |
| | A | B | A | B | A | B | A | B | A | B | A | B | A | B | A | B | A | B | |
| Hybridization | + | + | + | + | + | + | + | + | + | + | + | + | + | + | + | + | + | + | + |
| H2O | - | - | - | - | - | - | - | - | - | - | - | - | - | - | - | - | - | - | |
| E2A-PBX1 | + | + | - | - | - | - | - | - | - | - | - | - | - | - | - | - | - | - | + |
| AML1-ETO | - | - | + | + | - | - | - | - | - | - | - | - | - | - | - | - | - | - | + |
| BCR-ABL (p190) | - | - | - | - | + | + | - | - | - | - | - | - | - | - | - | - | - | - | + |
| BCR-ABL (p210) | - | - | - | - | + | - | + | + | - | - | - | - | - | - | - | - | - | - | |
| TEL-AML1 | - | - | - | - | - | - | - | - | + | + | - | - | - | - | - | - | - | - | + |
| MLL-AF4 | - | - | - | - | - | - | - | - | - | - | + | + | - | - | - | - | - | - | + |
| CBFB-MYH11 | - | - | - | - | - | - | - | - | - | - | - | - | + | + | - | - | - | - | + |
| SIL-TAL1 | - | - | - | - | - | - | - | - | - | - | - | - | - | - | + | + | - | - | + |
| PML-RARA | - | - | - | - | - | - | - | - | - | - | - | - | - | - | - | - | + | + | + |
| Translocations | E2A-PBX1 | | AML1-ETO | | BCR-ABL (p190) | | BCR-ABL (p210) | | TEL-AML1 | | MLL-AF4 | | CBFB-MYH11 | | SIL-TAL1 | | PML-RARA | | |

FIG. 11

| Samples | SBE primers | | | | | | | | | | | | | | | | | | | |
|---|---|---|---|---|---|---|---|---|---|---|---|---|---|---|---|---|---|---|---|---|
| | E2A-PBX1 | | AML1-ETO | | BCR1-ABL | | BCR2-ABL | | TEL-AML1 | | MLL-AF4 | | CBFB-MYH11 | | SIL-TAL1 | | PML-RARA | | RARA-actin |
| | A | B | A | B | A | B | A | B | A | B | A | B | A | B | A | B | A | B | |
| HL-60 cells | - | | - | | - | | - | | - | | - | | - | | - | | - | - | + |
| ML-1 cells | - | - | - | - | - | - | - | - | - | - | - | - | - | - | - | - | - | - | + |
| 697 cells | + | + | - | - | - | - | - | - | - | - | - | - | - | - | - | - | - | - | + |
| KASUMI-1 cells | - | - | + | + | - | - | - | - | - | - | - | - | - | - | - | - | - | - | + |
| K562 cells | - | - | - | - | - | - | + | + | - | - | - | - | - | - | - | - | - | - | + |
| REH cells | - | - | - | - | - | - | - | - | + | + | - | - | - | - | - | - | - | - | + |
| MV4-11 cells | - | - | - | - | - | - | - | - | - | - | + | + | - | - | - | - | - | - | + |
| RS4;11 cells | - | - | - | - | - | - | - | - | - | - | + | + | - | - | - | - | + | - | + |
| Translocations | E2A-PBX1 | | AML1-ETO | | BCR-ABL (p190) | | BCR-ABL (p210) | | TEL-AML1 | | MLL-AF4 | | CBFB-MYH11 | | SIL-TAL1 | | PML-RARA | | |

*FIG. 12*

| Parent transcript | | Oligo name | 5' position (strand) | Length (bp) | Sequence (5'-3') | |
|---|---|---|---|---|---|---|
| MLL | | MLL-T | 3946 | 45(+) | AGAAAAGAAGTTCCAAAACCACTCCTAGTGAGCCCAAGAAAAAG | SEQ ID NO:74 |
| AF4 | | AF4-T | 1623 | 45(+) | CCAAAAACAATATGATACATCTTCAAAAACTCACTCAAATTCTCA | SEQ ID NO:75 |
| MLL-AF4 fusion transcripts | e8-e7 | MLL-AF4-CT | 3996 | 45(+) | TCCACCACCAGAATCAGAACAATATCAGCAGACCTCCAATGAAGTC | SEQ ID NO:76 |
| | e8-e4 | MLL-AF4-DT | 3989 | 45(+) | AGCAGCCTCCACCACCAGAATCAGCAGACCTCCAATGAAGTC | SEQ ID NO:77 |
| | e9-e5 | MLL-AF4-ET | 4063 | 45(+) | GTAAAACAAAAACCAAAAGAAAAAGCAGACCTACTCCAATGAAGTCC | SEQ ID NO:78 |
| | e9-e4 | MLL-AF4-FT | 4064 | 45(+) | TAAAACAAAAACCAAAAGAAAAAGCAGACCTACTCCAATGAAGTCC | SEQ ID NO:79 |
| | e10-e6 | MLL-AF4-GT | 4195 | 45(+) | CACAGGATCAGAGTGACTTTAAGGACTTTCAGCATGTCAGTTCT | SEQ ID NO:80 |
| | e10-e5 | MLL-AF4-HT | 4195 | 45(+) | CACAGGATCAGAGTGGACTTTAAGGAAATGACCCATTCATGCCG | SEQ ID NO:81 |
| | e10-e4 | MLL-AF4-IT | 4194 | 45(+) | CCACAGGATGGAGTGGACTTTAAGCAGACCTACTACCAATGAAGT | SEQ ID NO:82 |
| | e11-e6 | MLL-AF4-JT | 4312 | 45(+) | GCCAGTAGTGGGCATGTAGAGGACTCTCAGCATGTCAGTTCTGTA | SEQ ID NO:83 |
| | e11-e5 | MLL-AF4-KT | 4307 | 45(+) | TCTGTGCCAGTAGTGGGCATGTAGAGGAAATGACCCATTCATGGC | SEQ ID NO:84 |
| | e11-e4 | MLL-AF4-LT | 4307 | 45(+) | TCTGTGCCAGTAGTGGGCATGTAGAGCAGACCTACTCCAATGAAG | SEQ ID NO:85 |
| β-actin | | Actin-T | 1000 | 45(+) | TGGCACCCAGCACAATGAAGATCAAGATCATTGCTCCTCCTGAGC | SEQ ID NO:86 |

*FIG. 13*

| Reaction | Template | Primer name | 5' position (strand) | Length (bp) | Sequence (5'-3') | |
|---|---|---|---|---|---|---|
| PCR primers | MLL-AF4 | MLL-F | 3916 (+) | 17 | CCGCCTCAGCCACCTAC | SEQ ID NO:87 |
| | | AF4-R | 1714 (-) | 20 | TGTCACTGAGCTGAAGGTCG | SEQ ID NO:88 |
| | β-actin | Actin-F | 699 (+) | 23 | GCCCTGGACTTCGAGCAAGAGAT | SEQ ID NO:89 |
| | | Actin-R | 1361 (-) | 23 | CCTCGGCCACATTGTGAACTTTG | SEQ ID NO:90 |
| SBE primers | MLL-AF4 | MLL-A | 3968 (-) | 20 | TCTCATGGCGAAACCGGAACTTTCTTGGGCTCACTAGGAG | SEQ ID NO:91 |
| | | AF4-B | 4025 (-) | 24 | ATATTTGGCGGGAAACACGTAATTTGAGTGAGTTTTTGAAGATG | SEQ ID NO:92 |
| | | MLL-AF4-C | 4082 (-) | 42 | TGGTGAGATACCCGGGTTCACATGAATCATGGGTCATTTCCTTTT | SEQ ID NO:93 |
| | | MLL-AF4-D | 4212 (-) | 44 | GTCCGTTCCCTTAAGTGTGTTTCATTGAGTAGGTCTGCTTAAAG | SEQ ID NO:94 |
| | | MLL-AF4-E | 4326 (-) | 43 | TTGGGTCCTTCCGAGGGTACATGAATGGGTCATTTCCTCTACA | SEQ ID NO:95 |
| | | MLL-AF4-F | 4006 (-) | 43 | CTACCAAGTCGCCGAACACACATTGGAGTAGGTCTGCTGATTC | SEQ ID NO:96 |
| | | MLL-AF4-G | 4326 (-) | 44 | AACATCCCGGCCGTGGAACATGGAGTAGGTCTGCTCTACA | SEQ ID NO:97 |
| | | MLL-AF4-H | 4326 (-) | 44 | CAATGCCGTGGAAATCATTGGAGTAGGTCTGCTCTACA | SEQ ID NO:98 |
| | | MLL-AF4-I | 4009 (-) | 46 | CGTAGACAGCAAGGCCATTTTTGAAGATGTATCATATTGTTCTGA | SEQ ID NO:99 |
| | | MLL-AF4-J | 4080 (-) | 44 | AAGATGGCGCGCCAAATGCTTCGCTGACATGCTGAGAGTCTTTTCT | SEQ ID NO:100 |
| | | MLL-AF4-K | 4212 (-) | 44 | TAAATTGGCCAAATGCTTCGCTGACATGCTGAGAGTCCTTAAAG | SEQ ID NO:101 |
| | | MLL-AF4-L | 4212 (-) | 43 | CCTATCCTTTGGGCGAACTGATGAATGGGTCATTTCCTTAAAG | SEQ ID NO:102 |
| | β-actin | actin | 1018 (-) | 43 | TTAGAACGCCTTTAGCAGCCAGGAGGAGCAATGATCTTGATCT | SEQ ID NO:103 |

FIG. 14

| Samples | SBE primers ||||||||||||| |
| --- | --- | --- | --- | --- | --- | --- | --- | --- | --- | --- | --- | --- | --- |
| | MLL-A | MLL-AF4-C | MLL-AF4-D | MLL-AF4-E | MLL-AF4-F | MLL-AF4-G | MLL-AF4-H | MLL-AF4-I | MLL-AF4-J | MLL-AF4-K | MLL-AF4-L | AF4-B | AF4-actin |
| MLL-AF4-CT | + | + | - | - | - | - | - | - | - | - | - | + | + |
| MLL-AF4-DT | + | - | + | - | - | - | - | - | - | - | - | + | + |
| MLL-AF4-ET | + | - | - | + | - | - | - | - | - | - | - | + | + |
| MLL-AF4-FT | + | - | - | - | + | - | - | - | - | - | - | + | + |
| MLL-AF4-GT | + | - | - | - | - | + | - | - | - | - | - | + | + |
| MLL-AF4-HT | + | - | - | - | - | - | + | - | - | - | - | + | + |
| MLL-AF4-IT | + | - | - | - | - | - | - | + | - | - | - | + | + |
| MLL-AF4-JT | + | - | - | - | - | - | - | - | + | - | - | + | + |
| MLL-AF4-KT | + | - | - | - | - | - | - | - | - | + | - | + | + |
| MLL-AF4-LT | + | - | - | - | - | - | - | - | - | - | + | + | + |

*FIG. 15*

| Samples | SBE primers | | | | | | | | | | | | |
|---|---|---|---|---|---|---|---|---|---|---|---|---|---|
| | MLL-A | MLL-AF4-C | MLL-AF4-D | MLL-AF4-E | MLL-AF4-F | MLL-AF4-G | MLL-AF4-H | MLL-AF4-I | MLL-AF4-J | MLL-AF4-K | MLL-AF4-L | AF4-B | actin |
| ML-1 cells | - | - | - | - | - | - | - | - | - | - | - | - | |
| MV4-11 cells | + | + | - | - | - | - | - | - | - | - | - | - | + |
| RS4;11 cells | + | - | + | - | - | - | - | - | - | - | - | + | + |

*FIG. 16*

| Translocations | | Number of different known fusion transcripts |
|---|---|---|
| E2A-PBX1 | E2A-F → ... ← PBX1-R / 13 / 2 / E2A-A ← ... ← PBX1-B | 2 |
| MLL-AF4 | MLL-F → ... ← AF0-4-R / 8 / 7 / 8 / 9 / MLL-A ← ... ← AF4-B | 10 |
| AML1-ETO | AML1A-F → ... ← ETO-R / 1 / 2 / 3 / 4 / 5 / 2 / 3 / 4 / 5 / AML1-A ← ... ← ETO-B | 1 |
| BCR-ABL(p190) | BCR1-F → ... ← ABL-R / 1 / 3 / 4 / BCR1-A ← ... ← ABL-B | 2 |
| BCR-ABL(p210) | BCR2-F → ... ← ABL-R / 11 / 12 / 13 / 2 / 3 / 4 / BCR2-A ← ... ← ABL-B | 4 |
| TEL-AML | TEL-F → ... ← AML1B-R / 4 / 5 / 3 / 4 / 5 / 6 / TEL-A ← ... ← AML1-B | 2 |
| PML-RARA | PML-F → ... ← RARA-R / 3 / 3 / PML-A ← ... ← RARA-B | 3 |
| CBFB-MYH11 | CBFB-F → ... ← MYH11-R / 4 / 5 / 12 / 13 / 14 / CBFB-A ← ... ← MYH11-B | 3 |
| SIL-TAL1 | SIL-F → ... ← TAL1-R / 1a / 4 / 5 / SIL-A ← ... ← TAL1-B | 3 |

*FIG. 17*

EARLY LEUKEMIA DIAGNOSTICS USING MICROSPHERE ARRAYS

CROSS-REFERENCES TO RELATED APPLICATIONS

This application claims the benefit of U.S. Provisional Patent Application Ser. No. 60/335,716, filed Nov. 20, 2001 which is herein incorporated by reference in its entirety for all purposes.

REFERENCE TO A "SEQUENCE LISTING," A TABLE, OR A COMPUTER PROGRAM LISTING APPENDIX SUBMITTED ON A COMPACT DISK

Not applicable.

STATEMENT AS TO RIGHTS TO INVENTIONS MADE UNDER FEDERALLY SPONSORED RESEARCH OR DEVELOPMENT

This invention was made with Government support under Contract No. W-7405-ENG-36 awarded by the U.S. Department of Energy. The Government has certain rights in this invention.

BACKGROUND OF THE INVENTION

Chromosome translocations have been correlated with multiple diverse cancers including leukemia, lymphoma, breast cancer, renal cancer, peripheral neuroepithelioma, synovial carcinoma, and ganglioneuroblastomas (see, e.g., Onida et al., *Cancer* 95(8):1673–84 (2002); Million et al., *Blood* 99(12):4568–77 (2002); Popovici et al., *Genes Chromosomes Cancer* 35(3):204–18 (2002); Bodmer et al., *Cancer Genet Cytogenet.* 136(2):95–100 (2002); Podolski et al., *J Hum Genet.* 46(12):685–93 (2001); Dai et al., *Zhonghua Yi Xue Za Zhi* (Taipei) 65(6):293–7 (2002); Van Roy et al, *Genes Chromosomes Cancer* 35(2):113–20 (2002); Sossey-Alaoui et al., *Oncogene* 21(38):5967–74 (2002)). For example, since the discovery of the BCR-ABL fusion gene, more than 50 different consistently occurring translocations associated with leukemic cells have been identified (Pallisgaard et al., *Blood* 92:574–588 (1998)). These chromosomal structural rearrangements may directly or indirectly alter the activities of cellular proto-oncogenes, especially transcription factors, resulting in disturbance of the normal programs of cell proliferation, differentiation, and apoptosis (Look, *Science* 278:1059–1064 (1997)). These genes can play key roles in the development and function of cells, and their alteration may act in concert with other genetic changes in a multiple step pathway to result in oncogenic transformation.

For example, chromosome translocations are found in up to 65% of the acute leukemias, and the nature of these translocations can delineate patients with a defined prognosis. Clinical studies have shown that many of these translocations are specific for particular subtypes of leukemias, so that chromosome rearrangements can also be used for risk group classification in acute lymphoblastic leukemia and acute myeloid leukemia. This has greatly improved treatment of the acute leukemias by using a protocol tailored to the risk of relapse in discrete subgroups instead of uniform strategies for all patients ((Look, 1997, supra). Although routine clinical parameters, such as age, white blood cell count, and blast cell immunophenotype, provide useful criteria for risk assessment, the determination of chromosome rearrangement offers much more valuable prognosis information for cancer patients.

A number of assays have been developed for the determination of chromosome arrangement. For example, cytogenetic assays such as FISH (fluorescence in situ hybridization) are useful methods to detect chromosome translocations and can be valuable tools for cancer prognosis. However, cytogenetic assays are time- and labor-intensive, and require sufficient metaphase cells, which are difficult to obtain for some patient samples (Pallisgaard et al., 1998, supra and Popescu et al., *Cancer Genetics and Cytogenetics* 93:10–21 (1997)). Reverse transcriptase (RT)-polymerase chain reaction (PCR)-based assays to identify chromosome translocations have also been developed. RT-PCR based assays are much more sensitive than cytogenetic assays and can be performed on resting cells. However, for an unequivocal molecular diagnosis, RT-PCR-based methods must be augmented with hybridization probes or direct sequencing, adding to the time, cost, and technical complexity of the method. Thus, for early molecular diagnostics applications, especially initial characterization of patient samples, new tools are needed.

There has been increasing interest in the use of microparticle arrays for high throughput screening to detect genetic abnormalities, including chromosome translocations. The concept of using microspheres and flow cytometry to perform multiplexed assays was initially proposed by Horan and Wheeless, *Science* 198(4313):149–57 (1977), using different sized microspheres, and further developed recently using different colored microspheres (Fulton et al., *Clinical Chemistry* 43:1749–1756 (1997)). The use of microparticle arrays has been described for immunoassays, single nucleotide polymorphism (SNP) (see, e.g., U.S. Pat. No. 6,287,766), genotyping, bacterial signature detection, and detection of DNA or RNA viruses (Fulton et al., 1997, supra; Cai et al., *Genomics* 66:135–143 (2000); Nolan et al. 47th Annual Meeting of the American Society of Human Genetics, Oct. 28-Nov. 1, 1997 Baltimore Md.; Iannone et al., *Cytometry* 39:131–140 (2000); Vignali, *J. Immunological Methods* 243:243–255 (2000); Armstrong et al, *Cytometry* 40:102–108 (2000); and Defoort et al., *J. Clinical Microbiology* 38:1066–1071(2000)).

There is a need in the art for methods of identifying chromosome translocations and methods for diagnosing cancer. The present invention addresses this need.

BRIEF SUMMARY OF THE INVENTION

The present invention provides methods and kits for detecting chromosome translocations. The present invention further provides methods for diagnosing cancer, such as, for example, leukemia.

One embodiment of the present invention provides methods for detecting chromosome translocations. A target nucleic acid sequence is amplified from a biological sample. A first oligonucleotide specific for a first region of the translocation is hybridized to the amplified target under conditions in which the first oligonucleotide specifically hybridizes to the first region of the translocation. The first oligonucleotide typically comprises a first capture tag. A second oligonucleotide specific for a second region of the translocation is hybridized to the amplified target under conditions in which the second oligonucleotide specifically hybridizes to the second region of the translocation. The second oligonucleotide typically comprises a second capture tag. The first and second hybridized oligonucleotide sequences are extended to produce a first and a second labeled extended oligonucleotide. In some embodiments, the step of extending comprises adding a labeled dideoxynucleotide to the 3' end of the oligonucleotide. In some embodiments, the dideoxynucleotide has a fluorescent label. The first and second oligonucleotides are hybridized to a first and a second address tag on a solid support under conditions in which the first and second address tags specifically hybridize to the first and second capture tags. The presence of the first and second labeled extended oligonucleotides on the solid support is detected, thereby detecting the presence of the chromosome translocation. In some embodiments, the step of extending occurs on a solid support. In some embodiments, the step of extending precedes the step of hybridizing to an address tag on a solid support. In some embodiments, the first and second capture tags each comprise an oligonucleotide and the first and second address tags each comprise an oligonucleotide. In some embodiments, the first and second hybridized oligonucleotide sequences are extended by a single base. In other embodiments, the first and second hybridized oligonucleotide sequences are extended by multiple bases. In some embodiments, the first and second capture tags each comprise an oligonucleotide and the first and second address tags each comprise an oligonucleotide. In some embodiments, the target nucleic acid is a cDNA.

In some embodiments, a third oligonucleotide specific for a junction region within the translocation is hybridized to the amplified target under conditions in which the third oligonucleotide specifically hybridizes to the junction region. The third oligonucleotide typically comprises a third capture tag. The third hybridized oligonucleotide sequence is extended to produce a third labeled extended oligonucleotide. The third oligonucleotide is hybridized to a third address tag on a solid support under conditions in which the third address tag specifically hybridizes to the third capture tag. The presence of the third labeled extended oligonucleotide on the solid support is detected, thereby detecting the presence of the junction region. In some embodiments, the step of extending occurs on a solid support. In some embodiments, the step of extending precedes the step of hybridizing to an address tag on a solid support. In some embodiments, the third capture tag and the third address tag are oligonucleotides. In some embodiments, the third hybridized oligonucleotide is extended by a single base. In other embodiments, the third hybridized oligonucleotide sequences are extended by multiple bases.

In some embodiments, the solid support is a microparticle. In some embodiments, the microparticle has an optical property, such as, for example, color or fluorescence. In some embodiments, the microparticle is in a microarray. In other embodiments, the microparticle is in a suspension array. In some embodiments, the microparticles are microspheres. In some embodiments, the chromosome translocation is detected is by flow cytometry.

In some embodiments, the biological sample is from a human. In some embodiments, the chromosome translocation is associated with cancer. In some embodiments, the cancer is leukemia.

In some embodiments, the first oligonucleotide and second oligonucleotide comprises a pair of sequences selected from: SEQ ID NOS: 38 and 39, SEQ ID NOS: 40 and 41, SEQ ID NOS: 42 and 43, SEQ ID NOS: 44 and 45, SEQ ID NOS: 45 and 46, SEQ ID NOS: 47 and 48, SEQ ID NOS: 49 and 50, SEQ ID NOS: 51 and 52, and SEQ ID NOS: 53 and 54. In some embodiments, the third oligonucleotide is a sequence selected from: SEQ ID NOS: 93–102.

A further embodiment of the present invention provides a kit for detecting a chromosome translocation. The kit contains a first oligonucleotide specific for a first region of the translocation and a second oligonucleotide specific for a second region of the translocation. In some embodiments, the first and second oligonucleotides comprise the sequences set forth in SEQ ID NOS: 38–54. Each oligonucleotide comprises a capture tag comprising a polynucleotide sequence. In some embodiments, the kit further comprises a third oligonucleotide specific for a junction region within the translocation. In some embodiments, the third oligonucleotide comprises the sequences set forth in SEQ ID NOS: 93–102. In some embodiments, the kit further comprises an instruction manual.

Another embodiment of the present invention provides a method of diagnosing cancer. A target nucleic acid is amplified from a biological sample. A first oligonucleotide specific for a first region of the translocation is hybridized to the amplified target under conditions in which the first oligonucleotide specifically hybridizes to the first region of the translocation. The first oligonucleotide typically comprises a first capture tag. A second oligonucleotide specific for a second region of the translocation is hybridized to the amplified target under conditions in which the second oligonucleotide specifically hybridizes to the second region of the translocation. The second oligonucleotide comprises a second capture tag. A third oligonucleotide specific for a junction region within the translocation is hybridized to the amplified target under conditions in which the third oligonucleotide specifically hybridizes to the junction region. The third oligonucleotide comprises a third capture tag. The first, second, and third hybridized oligonucleotide sequences are extended to produce a first, second, and third labeled extended oligonucleotide. The first, second, and third oligonucleotides are hybridized to a first, a second, and a third address tag on a solid support under conditions in which the first, second, and third labeled extended oligonucleotides specifically hybridize to the first, a second, and a third address tag. The presence of the first, second, and third labeled extended oligonucleotides on the solid support is detected, thereby detecting the presence of the chromosome translocation. In some embodiments, the step of extending occurs on a solid support. In some embodiments, the step of extending precedes the step of hybridizing to an address tag on a solid support. In some embodiments, the first, second, and third capture tags each comprise an oligonucleotide, and the second, and a third address tag each comprise an oligonucleotide. In some embodiments, the cancer is leukemia. In some embodiments, the first oligonucleotide and second oligonucleotide comprises a pair of sequences selected from the group consisting of S SEQ ID NOS: 38 and 39, SEQ ID NOS: 40 and 41, SEQ ID NOS:42 and 43, SEQ ID NOS: 44 and 45, SEQ ID NOS: 45 and 46, SEQ ID NOS: 47 and 48, SEQ ID NOS: 49 and 50, SEQ ID NOS: 51 and 52, and SEQ ID NOS: 53 and 54. In some embodiments, third oligonucleotide is a sequence selected from the group consisting of SEQ ID NOS: 93–102. In some embodiments, the solid support is an array. In some embodiments, the solid support is a microarray. In some embodiments, the solid support comprises at least two microparticles. In some embodiments, the microparticles have an optical property. In some embodiments, the microparticles are in a suspension array. In some embodiments, the step of extending comprises adding a labeled dideoxy nucleotide to the 3' end of the oligonucleotide. In some embodiments, the dideoxy nucleotide has a fluorescent label. In some embodiments, the step of detecting is by flow cytometry.

Other embodiments and advantages of the present invention will be apparent from the detailed description that follows.

BRIEF DESCRIPTION OF THE DRAWINGS

FIG. 2 depicts a schematic diagram for ten MLL-AF4 fusion transcripts with known junction sequences and the relative position of primers. The structures of ten MLL-AF4 fusion transcripts with known junction points are shown. The boxes are exons with the exon numbers inside. Dotted boxes represent exons from MLL, while open boxes represent exons from AF4. The numbers on the left indicate the particular exon of MLL and AF4 where the junction is found. The arrows above each box are PCR primers. MLL-F primer is complementary to the sequence of exon 8 of MLL, while AF4-R is complementary to the sequence of exon 8 of AF4. The arrows below each box are SBE primers. MLL-A and AF4B are complementary to MLL and AF4, respectively, and are consensus sequences for all known MLL-AF4 fusion transcripts. MLL-AF4-C, D, E, F, G, H, I, J, K, L are complementary with the junction sequence of all ten known MLL-AF4 fusion transcripts.

FIG. 7 shows the sequences of templates for translocations (SEQ ID NOS:1–18).

FIG. 8 shows sequences of primers for amplifying translocations (SEQ ID NOS:19–37).

FIG. 9 shows sequences of primers comprising capture tags for single base extension (SEQ ID NOS:38–55).

FIG. 10 shows sequences of primers for single base extension (SEQ ID NOS:56–73).

FIG. 11 shows the results of detection of synthetic multi-translocations.

FIG. 12 shows the results of multiplex detection of translocations in cell lines.

FIG. 13 shows the sequences of templates for MLL-AF4 fusion transcripts (SEQ ID NOS:74–86).

FIG. 14 shows sequences of primers for amplifying MLL-AF4 fusion transcripts (SEQ ID NOS:87–106).

FIG. 15 shows the results of detection of synthetic MLL-AF4 fusion transcripts.

FIG. 16 shows the results of detection of MLL-AF4 in cell lines.

FIG. 17 illustrates the structures of nine known translocations. Each numbered box represents an exon. Dotted boxes are exons derived from one gene, while open boxes illustrate exons from the other gene of the same translocation. The name of translocation is listed on the left. The numbers on the right indicate the number of transcription variants that have been found for the particular translocation. The arrows above each box are PCR primers. The arrows below each box are SBE primers.

DETAILED DESCRIPTION OF THE INVENTION

I. Introduction

Figure 1:
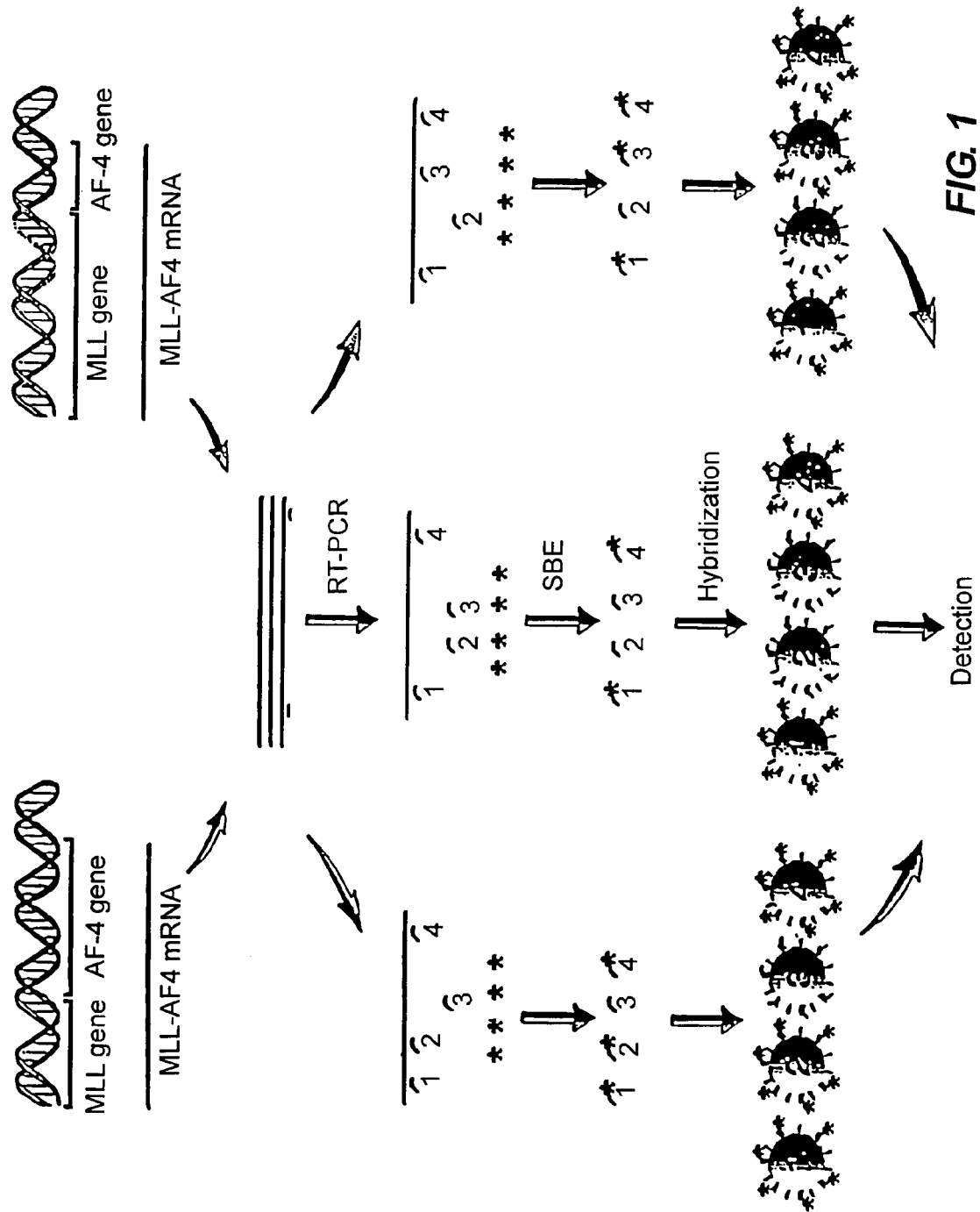
FIG. 1 depicts an exemplary strategy for detecting MLL-AF4 translocations. RNA samples are isolated from cell lines or patient samples and first strand cDNA synthesized by RT-PCT. PCR primers are designed to amplify all known fusion transcripts. SBE is carried out using the PCR products as templates. Two primer (1 and 4) with specific capture sequence tags are designed to complement all fusion transcripts. Primer 1 targets the part from the MLL gene. Primer 4 targets the part from the AF4 gene. Unique primers (2 or 3) with different capture tags are designed for the junction sequence of each fusion transcript. In the reaction containing a fusion transcript with known junction sequences (left), the consensus primers (1 and 4) and the specific junction primer (2) will be extended with fluorescein labeled dideoxy nucleotides, but the other junction primer (3) will not. In the reaction containing a fusion transcript with known junction sequences (right), the consensus primers (1 and 4) and the specific junction primer (3) will be extended with fluorescein labeled dideoxy nucleotides, but the other junction primer (2) will not. In the reaction containing a fusion transcript with unknown junction sequences (center), only the consensus primers (1 and 4) will be extended with fluorescein labeled dideoxy nucleotides

The present invention provides methods and kits for the detection of chromosome translocations. In particular, this invention provide methods for diagnosis of cancers associated with chromosome translocations, such as leukemia and lymphoma.

II. Definitions

"Chromosome translocation" as used herein refers to a rearrangement in which part of a first chromosome and part of a second chromosome are detached by breakage and then becomes attached to each other. The point at which the first and second chromosome are attached to each other is known as the "junction region" or "translocation junction." Each junction region comprises a first gene from the first chromosome and a second gene from the second chromosome. The methods of the present invention can conveniently be used to detect junction regions that are transcribed as fusion transcripts.

A "target sequence" or "target nucleic acid sequence" refers to a single or double stranded polynucleotide sequence sought to be amplified in an amplification reaction. Typically, a target nucleic acid sequence is a chromosome translocation. Two target sequences are different if they comprise non-identical polynucleotide sequences.

An "amplification reaction" refers to any chemical reaction, including an enzymatic reaction, which results in increased copies of a template nucleic acid sequence. Amplification reactions include polymerase chain reaction (PCR) and ligase chain reaction (LCR) (see U.S. Pat. Nos. 4,683,195 and 4,683,202; PCR Protocols: A Guide to Methods and Applications (Innis et al., eds, 1990)), reverse-transcriptase PCR (RT-PCR) (Sambrook and Russell, MOLECULAR CLONING, A LABORATORY MANUAL (3rd ed. 2001).

The term "primer" refers to a nucleic acid sequence that specifically anneals to the target nucleic acid sequence and primes the synthesis of a polynucleotide in an amplification reaction. Typically a primer comprises fewer than about 100 nucleotides, preferably fewer than about 60 nucleotides, more preferably fewer than 40 nucleotides. Exemplary primers range from about 10 to about 40 nucleotides, from about 12 to about 35 nucleotides, or from about 15 to about 25 nucleotides. One of skill in the art will appreciate that primer length can be adjusted depending on the annealing temperature and amplification conditions without undue experimentation. A primer may further comprise a capture tag, i.e., a nucleic acid sequence that does not specifically anneal to the target nucleic acid sequence.

"Nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

"Capture tag" as used herein refers to a targeting moiety, typically a nucleic acid comprising a sequence that does not specifically hybridize or specifically anneal to a target nucleic acid, e.g., a region of a chromosome translocation. However, in some embodiments of the invention, the capture tag comprises the primer used in an extension reaction to detect the translocation junction. Often, a capture tag is located at the 5' end of an oligonucleotide (e.g., a primer) that specifically hybridizes to a chromosome translocation. In some embodiments of the present invention, the capture tag and the oligonucleotide are separated by a linker. Suitable linkers include, for example, carbon linkers as described in, e.g., Lukhtanov et al., *Bioconjug. Chem.*, 7: 564–567 (1996). One of skill in the art will appreciate that the linker can be any length and will be designed to minimize interference with the interaction between the capture tag and the address tag. Typically, the carbon linker will be between about 2 and about 25 carbons in length, more typically between about 4 and about 20 carbons in length, even more typically between about 5 and about 18 carbons in length, most typically between about 7 and about 15 carbons in length. A capture tag can be any length. Typically, a capture tag is about 10 to about 40 nucleotides in length, more typically about 15 to about 30 nucleotides in length, even more typically at least 18 to about 21 nucleotides in length. It will be appreciated by those of skill in the art that the capture tag may comprise the ligand component or the receptor component of any ligand-receptor combination known in the art, wherein the ligand and receptor specifically interact and bind each other. For example, in some embodiments of the invention, the capture tag comprises biotin. In other embodiments of the invention, the capture tag comprises one member of a coiled-coil pair. In further embodiments of the invention, the capture tag comprises an immunoglobulin molecule or an antigen binding portion thereof (see, e.g., Paul et al. FUNDAMENTAL IMMUNOLOGY 4th ed. 1999).

"Address tag" as used herein refers to a moiety, typically an oligonucleotide sequence that, specifically hybridizes to the capture tag. An address tag can be any length. Typically, an address tag is at least 10 nucleotides in length, more typically at least 15 nucleotides in length, even more typically at least 20 nucleotides in length. In some embodiments of the present invention, the address tag comprises a nucleotide sequence that is the reverse complement of the primer used in an extension reaction to identify a particular translocation junction, as described below. It will be appreciated by those of skill in the art that the address tag comprises the complement to the capture tag. For example, if a capture tag comprises the ligand component of a ligand-receptor combination, the corresponding address tag comprises the receptor component of the ligand-receptor combination. Conversely, if a capture tag comprises the receptor component of a ligand-receptor combination, the corresponding address tag comprises the ligand component of the ligand-receptor combination. As an illustrative example, in some embodiments of the present invention, the address tag comprises avidin or streptavidin. In other embodiments of the invention, the address tag comprises the member of a coiled-coil pair complementary to the capture tag. In further embodiments of the present invention, the address tag comprises an antigenic epitope recognized by a monoclonal antibody. Additional suitable address tags include peptide nucleic acids (pNAs) and locked nucleic acids (lNAs).

"Multiplex amplification" refers to amplification of multiple target polynucleotide fragments in the same reaction. Primer sets specific for multiple translocations are used in the same reaction for amplification of chromosome translocations. It will be appreciated by those of skill in the art that only those translocations actually present in the target polynucleotide will be amplified by the multiplex amplification reaction.

"Solid support" as used herein refers to any material to which an oligonucleotide can be attached or any material that can be modified so that an oligonucleotide can be attached to it. Solid supports are amenable to at least one detection method, e.g., an optical detection method. Solid supports may be planar or may have three dimensional structure. Suitable materials for a solid support include, for example, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, optical fiber bundles, and a variety of other polymers. A wide variety of organic and inorganic polymers, as well as other materials, both natural and synthetic, can be employed as the material for the solid surface or solid support. Illustrative solid surfaces or solid supports include, e.g., nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition, substances that form gels can be used. Such materials include, e.g., proteins (e.g., gelatins), lipopolysaccharides, silicates, agarose and polyacrylamides. Where the solid surface or solid support is porous, various pore sizes may be employed depending upon the nature of the system.

"Microparticle" as used herein refers to any particle that can conveniently be used as a solid support according to the methods of the present invention. Suitable microparticles include, for example, microspheres, smartbeads, smart dust, and other nanofabricated particles. Often, microparticles useful in the methods of the present invention possess an extrinsic optical property, e.g., color or fluorescence. In some embodiments, microparticles possess an extrinsic non-optical property, e.g., size gradation or shape. Exemplary microparticles are described in, e.g., WO 02/065123; WO 02/064829; WO 01/25002; WO 01/25758; and U.S. Patent Publication No. 20020119470 A1.

"Optical property" as used herein refers to an ability to interact with light waves, i.e., to absorb, refract, or reflect light waves. Optical properties include, for example, color, fluorescence, luminescence, brightness, transmittance or reflectance. "Fluorescent" or "fluorescence" refers to luminescence that is caused by the absorption by a molecule of incident radiation at one wavelength followed by nearly immediate reradiation by the molecule usually at a different wavelength. Fluorescence ceases almost at once when the incident radiation stops. "Luminescent" or "luminescence" as used herein refers to the low-temperature emission of light by a chemical or physiological process, i.e., chemiluminescence or bioluminescence. "Reflectance" or "reflectivity" refers to the fraction of the total radiant flux incident upon a surface that is reflected. Reflectance varies depending on the wavelength distribution of the incident radiation. "Transmittance" refers to the fraction of radiant energy reaches the boundary of a layer of absorbing matter.

"Specifically hybridizes" or "selectively hybridizes" as used herein refers to the binding or hybridizing of an oligonucleotide to a particular nucleotide sequence under appropriate hybridization conditions.

The phrase "stringent hybridization conditions" refers to conditions under which an oligonucleotide will hybridize to its target nucleic acid sequence (e.g., primer to translocation junction or capture tag to address tag), typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion (or other salts), typically about 0.001 to 1.0 M sodium ion, more typically about 800 nM sodium ion at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as follows: ramp temperature 2° C./sec to 80° C., 75° C. for 1 min, 70° C. for 1 min, 65° C. for 1 min, 60° C. for 1 min, 55° C. for 1 min, 50° C. for 1 min, 40° C. for 1 min 35° C. for 1 min, 30° C. for 1 min, and 25° C. for 1 min. After hybridization, the solution is held at 4° C. prior to wash with NaCl solution.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of about 30 seconds to about 2 minutes at 90° C.–95° C., an annealing phase of about 5 seconds to about 2 minutes at 50° C.–70° C., and an extension phase of about 1 minute to about 5 minutes at about 70° C.

"Biological sample" as used herein is a sample of biological tissue or fluid including animal and human body fluids such as whole blood, lymph fluids, lymphocytes, lymph nodes, fixed tissue specimens; and fixed cell specimens. Biological samples may also include sections of tissues such as biopsy and autopsy samples or frozen sections taken for histologic purposes. A biological sample is typically obtained from a mammal such as a primate e.g., chimpanzee or human; cow; dog; cat; a rodent, e.g., guinea pig, rat, mouse; rabbit. A biological sample may be suspended or dissolved in liquid materials such as buffers, extractants, solvents and the like.

III. Identification of Chromosome Translocations

One embodiment of the invention provides methods for detecting chromosome translocations. In particular, the invention provides methods for detecting translocation junctions. In some embodiments, the particular chromosome translocation is identified, then the particular translocation junction associated with that chromosome translocation is identified. In other embodiments of the invention, the chromosome translocation and the particular translocation junction associated with the chromosome translocation are identified simultaneously. In preferred embodiments of the invention, the methods of the present invention are used to diagnose cancers, including, for example, leukemia, lymphoma, breast cancer, renal cancer, peripheral neuroepithelioma, synovial carcinoma, and ganglioneuroblastomas. It will be appreciated by those of skill in the art that the methods of the present invention can be used to diagnose any cancer associated with a chromosome translocation. It will also be appreciated by those of skill in the art that the methods of the present invention can be used in a multiplex strategy to analyze multiple samples in parallel (see, e.g., U.S. Pat. Nos. 6,270,973; 6,280,618; 6,287,766; and 6,361,9506).

A. Amplification of Target Nucleic Acid Sequence

A target nucleic acid sequence (e.g., the region of a chromosome translocation that comprises the translocation junction) is amplified. Amplification of an RNA or DNA template using reactions is well known (see U.S. Pat. Nos. 4,683,195 and 4,683,202; Sambrook and Russell, 2001, supra; CURRENT PROTOCOLS IN MOLECULAR BIOLOGY (Ausubel et al., eds., John Wiley & Sons, Inc. 1994–1997, 2001 version); PCR TECHNOLOGY: PRINCIPLES AND APPLICATIONS FOR DNA AMPLIFICATION (Erlich, ed., 1992); PCR PROTOCOLS: A GUIDE TO METHODS AND APPLICATIONS (Innis et al., eds, 1990)). Methods such as polymerase chain reaction (PCR) and reverse-transcriptase (RT-PCR) can be used to amplify target nucleic acid sequences directly from cDNA, from genomic libraries, cDNA libraries, or from RNA (e.g., total RNA or mRNA).

Genomic DNA can conveniently be isolated from biological samples (e.g., obtained from leukemia or lymphoma patients) and PCR can be used to amplify DNA comprising the chromosome translocation (see, e.g., Sambrook et al., 2001, supra). Briefly, a target nucleic acid comprising the region of a chromosome translocation that comprises the translocation junction, is combined with a primer specific for the first region of the chromosome translocation corresponding to a first gene and a primer specific for a second region of a chromosome translocation corresponding to a second gene, dNTPs, Taq polymerase, and other reaction components. See Innis et al. The first and second gene define the region of the chromosome translocation corresponding to the first chromosome and the second chromosome, respectively. Typically primers are present at a concentration of about 100 nM to about 1 μM, more typically about 150 nM to about 700 nM, more typically about 175 nM to about 500 nM, most typically about 200 nM to about 400 nM. One of skill in the art will appreciate that the primer concentration can be empirically optimized to maximize the efficiency and specificity of the amplification reaction without undue experimentation. For example, some primers will be present at a concentration of about 800 nM. The primers specifically anneal to a first and second region of the chromosome translocation and, if the chromosome translocation is present, amplification of DNA comprising the chromosome translocation occurs.

Alternatively, mRNA can conveniently be isolated from biological samples (e.g., obtained from leukemia or lymphoma patients) and RT-PCR can be used to synthesize cDNA comprising the sequence resulting from the chromosome translocation (see, e.g., Sambrook et al., 2001, supra). It will be appreciated by those of skill in the art that both specific primers and random primers can conveniently be used to synthesize the cDNA sequence resulting from the chromosome translocation. Once the cDNA is synthesized specific primers are used in the extension reactions described below. Briefly, a target nucleic acid comprising the region of a chromosome translocation that comprises the translocation junction, is combined with a primer specific for the first region of the chromosome translocation corresponding to a first gene and a primer specific for a second region of a chromosome translocation corresponding to a second gene, dNTPs, reverse transcriptase, and other reaction components. See Innis et al., supra. The first and second gene define the region of the chromosome translocation corresponding to the first chromosome and the second chromosome, respectively. Typically primers are present at a concentration of about 100 nM to about 1 μM, more typically about 150 nM to about 700 nM, more typically about 175 nM to about 500 nM, most typically about 200 nM to about 400 nM. One of skill in the art will appreciate that the primer concentration can be empirically optimized to maximize the efficiency and specificity of the amplification reaction without undue experimentation. For example, some primers will be present at a concentration of about 800 nM. The primers specifically anneal to a first and second region of the chromosome translocation and, if transcripts of the chromosome translocation are present, amplification of cDNA comprising the chromosome translocation occurs.

In preferred embodiments of the present invention, multiplex amplification is used to amplify the target nucleic acid sequences. One of skill in the art will appreciate that primers that correspond to particular chromosome translocations can be designed for use in the methods of the present invention. For example, multiple sets of the primers shown in FIG. 7 can conveniently be used in a single reaction mixture to amplify any nucleic acid sequences corresponding to E2A-PBX1, MLL-AF4, AML1-ETO, BCR-ABL (p190), BCR-ABL (p210), TEL-AML1, PML-RARA, CBFB-MYH11, SIL-TAL1 chromosome translocations. Multiple sets of the primers shown in FIG. 13 can conveniently be used in a single reaction mixture to hybridize to nucleic acid sequences corresponding to translocation junctions of MLL-AF4 chromosome translocations. It will be appreciated by those of skill in the art that multiplex amplification will amplify only those chromosome translocations or translocation junctions actually present in the target nucleic acid sequences.

The reaction is preferably carried out in a thermal cycler to facilitate incubation times at desired temperatures. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

B. Detection of Hybridized Oligonucleotide Sequences

Once the cDNA or genomic DNA comprising the chromosome translocation is amplified, the cDNA or genomic DNA can conveniently serve as the template for a primer extension reaction that is used to identify the particular translocation junction (i.e., fusion transcript) present in the sample. Oligonucleotide sequences (e.g., primers) that specifically hybridize to portions of the translocation (e.g., portions of the translocation derived from the first gene, portions of the translocation derived from the second gene, or the translocation junction itself) are annealed to the cDNA and the oligonucleotide sequences are extended.

To increase the specificity of the extension reaction, the oligonucleotide primers that specifically hybridize to portions of the translocation derived from the first gene and portions of the translocation derived from the second gene are designed to specifically hybridize to a region of the first gene and a region of the second gene that are closer to the translocation junction than the primers used to amplify the translocation. In a preferred embodiment, the primers used in the extension reaction bind to a region of the translocation that does not overlap with the region of the translocation bound by the primers used to amplify the translocation. For example, if 20 base primer is used for the amplification reaction, the primer for the extension reaction will bind to a portion of the translocation that does not overlap with the region of the translocation bound by the 20 base primer. It will be appreciated by those of skill in the art, however, that some overlap between the extension primers and the amplification primers will not substantially affect the specificity of the extension reaction.

Typically, oligonucleotide primers that specifically hybridize to the translocation junction itself are used to identify translocation junctions. The primers are designed such that that they will only hybridize to the amplified cDNA or genomic DNA if the translocation junction is present; if the translocation junction is not present in the amplified cDNA or genomic DNA, the primers will not hybridize to it. Typically, the primers are designed so that the middle of the primer hybridizes to the translocation junction. For example, a 20 nucleotide primer may be aligned to hybridize to a translocation junction so that 10 nucleotides hybridize to the portion of the translocation derived from first gene and 10 nucleotides hybridize to the portion of the translocation derived from second gene. One of skill in the art will appreciate, however, that such a precise alignment is not a critical aspect of the invention. For example, 20 nucleotide primer will hybridize to a translocation junction so that 19, 18, 17, 16, 15, 14, 13, 12, 11, 10, 9, 8, 7, 6, 5, 4, 3, 2, or 1 nucleotides hybridize to the portion of the translocation derived from first gene and 1, 2, 3, 4, 5, 6, 7, 8, 9, 10, 11, 12, 13, 14, 15, 16, 17, 18, or 19 nucleotides hybridize to the portion of the translocation derived from second gene, respectively. Primers can be designed using any means known in the art, including, for example, commercially available and custom software such as OLIGO6. Typically, the software will use algorithms so that annealing temperatures are close to melting temperature. Preferably, all of the primers are designed so that they are compatible in a multiplex extension reaction.

The oligonucleotide sequences (e.g., primers) comprise a sequence that hybridizes to a chromosome translocation and a capture tag. In some embodiments, a capture tag is a sequence that does not hybridize to a chromosome translocation. A capture tag may also be the primer itself. Typically, a capture tag is located at the 5' end of the oligonucleotide. A capture tag can be any length. Typically, a capture tag is about 10 to about 40 nucleotides in length, more typically about 15 to about 30 nucleotides in length, even more typically at least 18 to about 21 nucleotides in length. In some embodiments of the present invention, the capture tag and the oligonucleotide are separated by a linker. Suitable linkers include, for example, carbon linkers as described in, e.g., Lukhtanov et al., *Bioconjug. Chem.,* 7: 564–567 (1996). One of skill in the art will appreciate that the linker can be any length and will be designed to minimize interference with the interaction between the capture tag and the address tag. Typically, the carbon linker will be between about 2 and about 25 carbons in length, more typically between about 4 and about 20 carbons in length, even more typically between about 5 and about 18 carbons in length, most typically between about 7 and about 15 carbons in length. Typically, capture tags specifically hybridize to address tags, a moiety, typically an oligonucleotide sequence that, specifically hybridizes to the capture tag. An address tag can be any length. Typically, an address tag is at least 10 nucleotides in length, more typically at least 15 nucleotides in length, even more typically at least 20 nucleotides in length. In some embodiments of the present invention, the-address tag comprises a nucleotide sequence that is the reverse complement of the primer used in an extension reaction to identify a particular translocation junction, as described above.

A labeled, extended oligonucleotide is formed from each oligonucleotide only if the respective translocation or translocation junction was present in the original nucleic acid sample. The oligonucleotides corresponding to different translocation junctions further comprise capture tags. Each capture tag comprises a unique sequence that is complementary to all or part of a corresponding address oligonucleotide. The use of a unique capture tag for each translocation junction increases the efficiency of detection of the chromosome translocation. For example universal arrays can be used with any primers or combination or primers provided that the primers comprise a capture tag that binds an address tag on the array. Furthermore, the use of capture tags eliminates interference from unreacted amplification primers and partially extended products.

1. Extension of the Hybridized Oligonucleotide Sequences

In some embodiments of the present invention, the hybridized oligonucleotide sequences are extended by a single base using single base extension (SBE) (see, e.g., Sylvanen et al, *Genomics* 8:684–692 (1990); U.S. Pat. Nos. 5,846,710 and 5,888,819; Pastinen et al., *Genomics Res.* 7(6):606–614 (1997)). SBE is a technique that utilizes an extension primer that hybridizes to the target nucleic acid. A polymerase (generally a DNA polymerase) is used to extend the 3' end of the primer with a nucleotide analog labeled a detection label as described herein. Based on the fidelity of the enzyme, a nucleotide is only incorporated into the extension primer if it is complementary to the adjacent base in the target nucleic acid. Often, the nucleotide is derivatized such that no further extensions can occur after a single nucleotide is added.

The reaction is initiated by combining the target sequence (e.g., the amplified cDNA or genomic DNA comprising the chromosome translocation), primers specific for the translocation junctions, and a solution comprising a dideoxy-nucleoside-triphosphate (ddNTP), e.g., ddATP, ddCTP, ddGTP and ddTTP or ddUTP. Typically, the ddNTP is labeled, e.g., with a molecule or moiety that is capable of being detected. The labels may be the same or different. Suitable labels include, for example, radioisotopes (e.g., $^{32}$P, $^{35}$S, $^{3}$H, $^{125}$I), fluorophores, chemiluminophores, colloidal particles, fluorescent dyes (see, e.g., U.S. Pat. No. 6,403,807) and non-fluorescent dyes.

In addition to a first nucleotide, the extension solution also comprises an extension enzyme, generally a DNA polymerase. Suitable DNA polymerases include any conventional or thermostable DNA polymerase such as, for example, the Klenow fragment of DNA polymerase I, SEQUENASE 1.0 and SEQUENASE 2.0 (U.S. Biochemical), Thermosequenase (Amersham), T5 DNA polymerase and Phi29 DNA polymerase. If the NTP is complementary to the base of the translocation junction, which is immediately adjacent (i.e., one nucleotide away from the junction) to the oligonucleotide annealed to the target nucleic acid, the extension enzyme will add the NTP to the oligonucleotide. Thus, the oligonucleotide is modified, i.e. extended, to form a modified oligonucleotide which can be detected as described below.

In some embodiments of the present invention, the first and second hybridized oligonucleotide sequences are extended by multiple bases using "labeled chain extension." The reaction is initiated by combining the target sequence (e.g., the amplified cDNA or genomic DNA comprising the chromosome translocation), primers specific for the translocation junction and comprising a capture tag, and a solution comprising a labeled (e.g., with a fluorescent label) deoxynucleoside-triphosphate (dNTPs), e.g., dATP, dCTP, dGTP and dTTP or dUTP. Multiple labeled dNTP's will be added to the end of the oligonucleotide, thus increasing the amount of signal present on the extended oligonucleotide sequence.

2. Ligation

In some embodiments of the present invention, ligation is used to detect the presence of translocation junctions. The first and second hybridized oligonucleotide sequences are typically designed to hybridize to two adjacent portions of a chromosome translocation. For example, the first oligonucleotide may specifically hybridize to the translocation junction and the second oligonucleotide may specifically hybridize to a conserved region of one gene of the chromosome translocation adjacent to the translocation junction. Alternatively, the two oligonucleotides may specifically hybridize to adjacent portions of the translocation junction. If the translocation junction is present, both oligonucleotides will hybridize to the target nucleic acid sequence and can be ligated to each other (see, e.g., U.S. Pat. No. 6,287,766). Typically one of the oligonucleotides is labeled, e.g., with a fluorescent label; and the other oligonucleotide comprises a capture tag. The ligated primers can be hybridized to an address tag and the chromosome translocation detected as described below.

3. Multiplex Reactions

In preferred embodiments of the present invention, multiplex extension is used to extend the hybridized oligonucleotide sequences (see, e.g., U.S. Pat. Nos. 6,287,766; 5,814,491). One of skill in the art will appreciate that primers that correspond to particular chromosome translocations and translocation junctions can be designed for use in the methods of the present invention. For example, multiple sets of the oligonucleotides shown in FIG. 9 can conveniently be used in a single reaction mixture to extend oligonucleotide sequences corresponding to E2A-PBX1, MLL-AF4, AML1-ETO, BCR-ABL (p190), BCR-ABL (p210), TEL-AML1, PML-RARA, CBFB-MYH11, SIL-TAL1 chromosome translocations and multiple sets of the primers shown in FIG. 14 can conveniently be used in a single reaction mixture to amplify nucleic acid sequences corresponding to MLL-AF4 chromosome translocations and translocation junctions.

As will be appreciated by those in the art, the configuration of both of the extension reactions can take on several forms. For example, the extension reactions may be done in solution, the labeled, extended oligonucleotides can be bound via their capture tags to address tags bound to microparticles, and the labeled, extended oligonucleotides can be detected. Alternatively, the extension reaction can occur on a solid support. For example, the oligonucleotides can be bound via their capture tags to address tags bound to microparticles. The oligonucleotides bound to microparticles can then be added to an extension reaction mixture comprising the amplified target nucleic acid. After the extension reaction, any labeled, extended oligonucleotides attached to the microparticles can be detected.

IV. Detecting the Chromosome Translocation

Once the oligonucleotides annealed to the target nucleic acid have been extended or the oligonucleotides have been ligated, the labeled extended oligonucleotides or ligated oligonucleotides are detected, thereby detecting the presence of the chromosome translocation and identifying particular translocation junctions. The labeled, extended oligonucleotides or ligated oligonucleotides can be detected using any means known in the art. Typically, the labeled extended oligonucleotides or ligated oligonucleotides are bound to a solid support, e.g., a microparticle and detected. Typically, microparticles useful in the methods of the present invention possess an extrinsic optical property such as, for example, color, fluorescence, luminescence, or brightness. Exemplary microparticles are described in, e.g., WO 02/065123; WO 02/064829; WO 01/25002; WO 01/25758; U.S. Patent Publication No. 20020119470 A1.

Many methods for immobilizing nucleic acids (e.g., address oligonucleotides) onto a variety of solid surfaces or solid supports are known in the art. In preparing the surface, a plurality of different materials may be employed, particularly as laminates, to obtain various properties. For example, proteins (e.g., bovine serum albumin) or mixtures of macromolecules (e.g., Denhardt's solution) can be employed to avoid non-specific binding, simplify covalent conjugation, enhance signal detection or the like. If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like.

Often, the microparticles are encoded or positioned to form a microarray. Among the various microarray-based molecular analysis tools, the use of microparticle arrays is gaining attention, especially for high throughput applications. The concept of using microspheres and flow cytometry to perform multiplexed assays was initially proposed by Horan and Wheeless, *Science* 198(4313):149–57 (1977), using different sized microspheres, and further developed recently using different colored microspheres (Fulton et al., *Clinical Chemistry* 43:1749–1756 (1997)). Microparticles may have different optical properties (e.g., fluorescence or light scatter) that can be discriminated by the flow cytometer. For example, using two fluorescent dyes incorporated into microparticles in different amounts, nearly a hundred different optically encoded microparticles can be identified. A specific molecular reaction is configured on the surface of each microparticle subset. After the reaction, microparticles are identified and the fluorescent signals for each reaction are measured using flow cytometry. Microsphere arrays have been successfully used for immunoassays, single nucleotide polymorphism (SNP), genotyping, bacterial signature detection, and detection of DNA or RNA viruses (Fulton et al., 1997, supra; Cai et al, *Genomics* 66:135–143 (2000); Nolan et al. 47th Annual Meeting of the American Society of Human Genetics, Oct. 28–Nov. 1, 1997 Baltimore Md.; Iannone et al., *Cytometry* 39:131–140 (2000); Vignali, *J. Immunological Methods* 243:243–255 (2000); Armstrong et al., *Cytometry* 40:102–108 (2000); and Defoort et al., *J. Clinical Microbiology* 38:1066–1071(2000)).

In a preferred embodiment, the microparticles are in a suspension array. "Suspension array" as used herein refers to an array comprising microparticles suspended in fluid (see, e.g., Nolan and Skar, *Trends in Biotech.* 20(1):9–12 (2002)). Typically, each microparticle in the array has a distinct optical property. Typically, a suspension array to be hybridized to the labeled, extended oligonucleotide sequences has about $10^4$ to about $10^{10}$ microparticles per ml, more typically about $10^6$ to about $10^8$ microparticles per ml, most typically about $10^7$ microparticles per ml. Any aqueous fluid that will not interfere with the optical analysis of the microparticles can be used in the array. Suitable fluids for a suspension array include, for example, saline, phosphate buffered saline, Tris buffer, or culture media for mammalian cells.

Analysis of the microparticles in a suspension array is typically done by flow cytometry (see, e.g., U.S. Pat. No. 6,287,766). Typically, the microparticles in the suspension array are diluted at least 10 fold, more typically at least 50 fold, most typically at least 100 fold before flow cytometry. Any aqueous fluid that will not interfere with the optical analysis of the microparticles can be used to dilute the microparticles before analysis. Suitable fluids for flow cytometry analysis include, for example, saline, phosphate buffered saline, Tris buffer, or culture media for mammalian cells. One of skill in the art will be able to select the degree of dilution and suitable fluids without undue experimentation.

One of skill in the art will appreciate that other methods of analyzing microparticles include, for example, fiber optic arrays in which beads are loaded into the end of a optic fiber and read using image analysis as is known in the art (see, e.g., U.S. Pat. Nos. 6,429,027; 6,396,995; 6,355,431; 5,250,264; and 5,244,636 and dipstick arrays in which beads are packed into a monolayer and read using image analysis as is known in the art (see, e.g., U.S. Pat. Nos. 6,197,598; 6,168,956; 6,146,833; 6,110,749; 6,087,184; 6,069,014; 6,017,767; 6,008,059; 5,998,220; and 5,981,185).

In some embodiments of the invention, the solid supports are include, for example, planar solid support (e.g. a glass surface, a membrane, etc.) or a high density microarray. Preparation and use of high density spotted arrays is described in, e.g., U.S. Pat. Nos. 6,428,957; 5,807,522; 5,143,854; Fodor et al., *Science* 767–773 (1991); WO 90/15070 and WO 92/10092.

In one embodiment of the invention, the labeled extended oligonucleotides are detected using flow cytometry. Methods and apparati for flow cytometry are described in, e.g., U.S. Pat. Nos. 6,382,228; 6,357,307; 6,287,766; 6,256,096; 6,248,590; and 5,540,494. For example, fluorescent signals on microparticles can be measured using a fluorescence activated cell sorter in conjunction with appropriate acquisition and analysis software. Colored microparticles can be gated using color compensation as is known in the art. The median fluorescence channel can be recorded for each subset of microparticles.

V. Kits

The present invention further provides kits for use in detecting chromosome translocations and diagnosing cancer. Such kits typically comprise a first oligonucleotide specific for a first region of the translocation and a second oligonucleotide specific for a second region of the translocation. In some embodiments, each oligonucleotide comprises a capture tag comprising a polynucleotide sequence. In some embodiments, the first and second oligonucleotides comprise the sequences set forth in SEQ ID NOS: 38–54. In some embodiments, the kits also include a third oligonucleotide specific for a junction region within the translocation. In some embodiments, the third oligonucleotide comprises the sequences set forth in SEQ ID NOS:93–102. Additional components of the kits may be compounds, reagents, containers, equipment, and/or instructions for using the components in accordance with the methods disclosed herein. For example, one container within a kit may contain address tags or address tags bound to a solid support such as, a microparticle. One or more additional containers may enclose elements, such as reagents or buffers, to be used in the assay. Other additional components that may be present within such kits include a reagent or container to facilitate the detection of a labeled, extended oligonucleotide using the methods of the present invention.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are offered to illustrate, but not to limit the claimed invention.

Example 1

Materials and Methods

Figure 3:
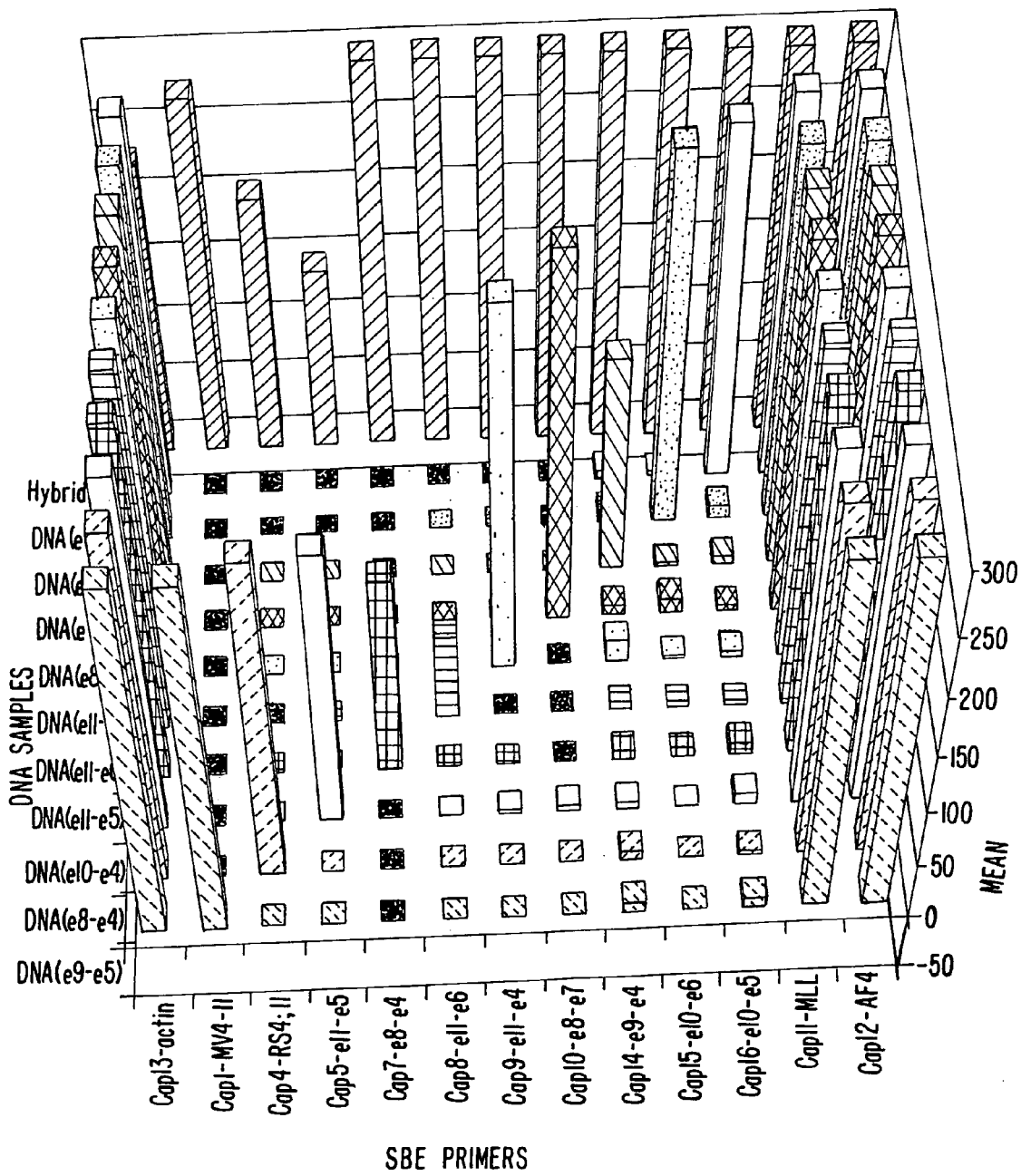
FIG. 3 depicts detection of synthesized MLL-AF4 DNA by SBE. Oligonucleotides comprising sequences from MLL, AF4, and actin were mixed with an oligonucleotide corresponding to the junction sequence of a particular fusion transcript. For example, DNA (e9-e5) contains oligonucleotides comprising sequences from MLL, AF4, actin, and e9-e5 and represents one MLL-AF4 fusion transcript (e9-e5). Signals generated by the hybridization of fluorescein labeled capture tags to the corresponding address tags on microspheres were detected. The Z-axis represents the mean fluorescence for each microsphere.

Primer design: Primers for multiplexed PCR and SBE (single base extension) were designed using program OLIGO 6 (Molecular Biology Insights, Inc., Cascade, Colo.). All DNA oligos were synthesized on an Applied Biosystems Model 394 oligonucleotide synthesizer using biotin-phosphoramidite and biotin- or amino-amino CPG from Glen Research (Sterling, Va.) or purchased from commercial sources. DNA oligos were desalted and their concentrations determined by absorbance at 260 nm. The PCR primers were designed to be able to amplify all known fusion transcripts for each translocation [FIG. 3, 5, (van Dongen et al., *Leukemia* 13:1901–1928 (1999))]. All PCR primers for nine translocations and the PCR primers for β-actin were designed to be multiplex compatible with each other. All SBE primers were designed to be able to extend one base U on their 3' end. All SBE primers are multiplex compatible, as confirmed by OLIGO 6.

Synthesized DNA templates for translocations: Eighteen oligonucleotides, each having 45 bases were synthesized (FIG. 7). Two oligos represent a single translocation: one oligonucleotide has the sequence derived from one gene; the other oligonucleotide has the sequence derived from the other gene of the same translocation. A 45 base oligonucleotide from β-actin was used for a control. For each of the nineteen oligonucleotides, we have designed a specific primer (FIG. 8). In each reaction tube, we mixed two oligonucleotides that represent a single translocation and an oligonucleotide for β-actin. A mixture of nineteen primers was added to each tube and the SBE reaction was performed.

Synthesized DNA templates for MLL-AF4 fusion transcripts: Twelve oligonucleotides, each having 45 bases were synthesized (FIG. 13). MLL-T is derived from MLL sequence, AF4-T from AF4 sequence, while other ten oligonucleotides are derived from the junction sequences of all ten known fusion transcripts (FIG. 13). A 45 base oligonucleotide for β-actin was used for a control. For each of these thirteen oligonucleotides, we have designed a specific primer (FIG. 14). Oligonucleotides for MLL-T, AF4-T, β-actin, and one oligonucleotide DNA for the junction sequence of a specific fusion transcript were mixed in a single tube. The mixture of MLL-DNA, AF4-DNA and one specific fusion junction DNA will represent a particular fusion transcript. A mixture of thirteen primers was added to each tube and the SBE reaction performed.

Culture of cell lines and RNA isolation: Cell lines 697, KASUMI-1, K562, REH, SD-1 and NB-4 were purchased from DSMZ-German Collection of Microorganisms and Cell Cultures (Braunschweig, Germany). Both 697 and REH cells are human B cell precursor leukemia. 697 cells contain translocation t(1;19) (q23; p13), while REH cells have translocation t(12; 21) (p13; q22). KASUMI-1 cells are human acute mycloid leukemia and contains translocation t(8;21) (q22; q22). K562 cells are human chronic myeloid leukemia in blast crisis and have translocation t(9;22) (q34; q11). SD-1 cells are human peripheral blood B-lymphoblastoid cells derived from patient with acute lymphoblastic leukemia and contain translocation t(9; 22) (q34; q11). NB-4 cells are human acute promyelocytic leukemia and have translocation t(15; 17) (q22; q21). CEM-C7-14 cells derived from CCRF-CEM cells are kindly provided by Dr. E. Brad Thompson (The University of Texas Medical Branch, Galveston, Tex.) and contain del (1) (p32; p32) translocation. All cell lines 697, KASUMI-1, K562, REH, SD-1 and NB-4, CEM-C7-14 and HL-60 were cultured in RPMI-1640 medium with 10% fetal bovine serum. MV4-11 and RS4;11 cell lines were purchased from ATCC (Manassas, Va.). MV4-11 cells are B myelomonocytic leukemia cells and cultured in Iscove's modified Dulbecco's medium with 4 mM L-glutamine containing 1.5 g/L sodium bicarbonate and 10% fetal bovine serum. RS4;11 cells are acute lymphoblastic leukemia cells and were cultured in Alpha modified minimum essential medium (Eagle) with 10% of fetal bovine serum. Both MV4-11 and RS4;11 cells have a characteristic chromosomal abnormality, t(4;11)(q21;q23), but containing different transcripts resulted from different break points. HL-60, kindly provided by Dr. Helan Cui (Bioscience Division, Los Alamos National Laboratory) and is a promyelocytic cell line derived by S. J. Collins, et al Peripheral blood leukocytes were obtained by leukophoresis from a 36-year-old Caucasian female with acute promyelocytic leukemia. In HL-60, HSR chromosomes were not detected. ML-1 cells are kindly provided by Dr. Karen LaRue (Bioscience Division, Los Alamos National Laboratory) and cultured in RPMI with 10% fetal bovine serum. ML-1 cells were derived from a patient with acute myeloid leukemia and have a translocation in t(6;11)(q27;q23) but not t(4;11) (q21;q23). Total RNA was isolated using the TRIzol Reagent according to the method provided by the manufacturer (GIBCO BRL, Gaithersburg, Md.).

RT-PCR amplification of MLL-AF4 fusion transcript and β-actin: In each reverse transcription reaction, 2.5 µg of total RNA and SuperScript™ II RNase H-reverse transcriptase from Life Technologies (Rockville, Md.) was used. Reverse transcription reaction was performed according to the manufacture instruction except that 1 µl of RNase inhibitor (Ambion, Inc., Austin, Tex.) was used in each reaction. PCR reaction was carried out according to the methods described van Dongen et al., *Leukemia* 13:1901–1928 (1999). The primer concentration for fusion transcripts is 800 nM, while primer concentration for β-actin is 50 nM.

PCR amplification of target nucleic acid sequence: Amplification reactions typically comprise: Amplification Reaction Mix Stock Solution: 7.8 mM $MgCl_2$, 2.1×Taq Polymerase Reaction Buffer, 210 mM dNTP Mix, 0.26 U/mL Taq DNA Polymerase, 526 nM each of the forward and reverse PCR primers, 1–3 copies Internal Control DNA. The final concentrations of the amplification reaction are typically 3.7 mM $MgCl_2$, 1×Taq Polymerase Reaction Buffer, 100 mM dNTP Mix, 12 U/mL Taq DNA Polymerase, 250 nM of the forward and reverse PCR primers, 475 copies control DNA. To start the reaction, 2.0 ml unknown sample or DNA, 9.5 ml Amplification Reaction Mix, and 8.5 ml $H_2O$ are combined and the desired product is amplified as follows: denaturation at 94° C. for 2 minutes followed by 40 cycles at 94° C. for 5 seconds, 57° C. for 10 seconds, then 70° C. for 5 minutes. The amplified product is typically held at 4° C. prior to, additional amplification, hybridization, or extension reactions.

Fluorescent chain extension(FCE): Fluorescent chain extension reactions (e.g., labeled chain extension reactions) comprise: 2×FCE Reaction Mix Stock Solution: 40 mM Tris-HCl (pH 8.4), 100 mM KCl, 2.5 mM $MgCl_2$, 50 nM of each FCE Capture oligonucleotides, 0.03 U Tsp DNA polymerase, and 5 µM TAMRA-dCTP. The final concentrations for the FCE reaction are typically: 20 mM Tris-HCl (pH 8.4), 50 mM KCl, 1.25 mM $MgCl_2$, 25 nM of each FCE Capture oligonucleotides, 0.015 U of Tsp DNA polymerase, and 2.5 µM TAMRA-dCTP. To start the reaction, 10 µl of amplified product is added to 10 µl FCE reaction mix and the amplified product is extended as follows: denaturation at 94° C. for 2 minutes, followed by 10 cycles at 94° C. for 40 seconds, 59° C. for 1 minute, 70° C. for 1 minute, then for 70° C. 5 minutes. After extension, the labeled, amplified product is held at 4° C. prior to hybridization (e.g., of capture tags to address tags).

Conjugation of oligonucleotides to microspheres: Carboxylated multiplex color microspheres were purchased from Luminex Corp. (Austin, Tex.). To conjugate address tag oligonucleotides to microspheres, microspheres were centrifuged for 2 minutes at 8000 rpm in an Eppendorf microcentrifuge, resuspended to $1\times10^8$/ml in 50 mM MES (2-[N-Morpholino] ethanesulfonic Acid, pH 6.5) with address tag oligos (final 10 µM), followed by addition of 1 mg of EDC (1 Ethyl-3-(3 dimethylaminopropyl) carbodiimide-HCl) and 0.1 mg of NHS (N-hydroxysuccinimide). The microsphere conjugation mixture was then mixed well and rotated for 15 minutes. One additional mg of EDC was added to the conjugation mixture, mixed well, and rotated over night with an aluminum foil cover. The mixture was washed with 400 µl MES, spun for 3 minutes at 8000 rpm, and resuspended to $1\times10^8$/ml with MES.

Single base extension assay: Before the SBE reaction, PCR products were cleaned-up with shrimp alkaline phosphatase (0.4 U/µl) and exonuclease 1 (0.4 U/µl) at 37° C. for 1 hour followed by 15 minutes at 72° C. to inactive the enzymes. For the SBE reaction, SAP/Exo-treated PCR product (7.5 µl) was mixed with primers (25 nM each), fluorescent dideoxynucleotide mix (non-fluorescent ddATP, ddGTP, ddCTP and fluorescent ddUTP, 7.5 µM each) and Thermosequenase (0.075 U/µl). The reaction was run in the PCR machine with initial denaturation at 94° C. for 2 minutes, followed by 99 cycles of 94° C. for 15 seconds and 60° C. for 15 seconds. The reaction products were mixed with the microspheres conjugated with corresponding address tags and NaCl (0.3 M) and incubated at room temperature for 30 minutes.

Fluorescence detection with flow cytometer: Fluorescence signals on microspheres were measured using Becton-Dickinson FACSCalibur (San Jose, Calif.) with CellQuest acquisition and analysis software or the Flowmetrix system (Luminex Corp., Austin, Tex.). interfaced with the FACSCalibur. Multiplex color microspheres were gated using color compensation. The median fluorescence channel was recorded for each microsphere subset. The background fluorescence signals of the microspheres from reactions without templates were subtracted for all samples.

Example 2

Identification of Translocation and Fusion Transcripts for the Translocation

FIG. 1 depicts identification of a translocation and fusion transcripts for the translocation. For illustrative purposes, identification of MLL-AF4 translocations (A) is described. MLL-AF4 gene is transcribed into fusion mRNA (B). The procedure includes three steps. The first step is RT-PCR amplification. Fusion transcripts are amplified with PCR primers which are designed to amplify all known transcription variants of MLL-AF4 translocation (C). The second step is hybridization and single base extension. Two primers (1 and 4) with specific capture sequence tags are designed to complement with the consensus sequence of the translocation. Primer 1 targets the portion of the translocation derived from MLL gene, while primer 4 targets the portion of the translocation derived from AF4 gene. Primers 2 and 3 are designed for another MLL-AF4 translocation. If the MLL-AF4 translocation is present in the sample, primers 1 and 4 will bind to the template, but primers 3 and 4 will not. The primers bound to the template will be extended with a fluorescence-labeled dideoxy nucleotide. This reaction is called single base extension (SBE) (D). Primer 2 and 3 will not be extended with fluorescence dye. The third step is capture and analysis. The labeled and unlabeled primers will then be hybridized to the complementary address tags immobilized on microspheres of different colors (E). The extrinsic fluorescence signals on the surface of the microspheres are then analyzed by flow cytometry. Detecting any fluorescence signal on each microsphere should identify the fluorescence extended primers and, thus, identify whether the sample contains a translocation. Once the presence of a translocation is determined, the fusion transcript variants for the translocation will be identified. For example, two MLL-AF4 fusion transcripts, each with different junction sequence ((D) and (H)). In addition to two consensus primers, 1 and 4, a unique primer (5 or 6) with different capture tag is designed for the specific junction sequence of each fusion transcript. In both cases, primer 1 and 4 will bind to the template. However, in the reaction on the left, the specific junction primer 5 will bind to the template, but the other junction primer 6 will not. In the reaction on the right, the specific junction primer 6 will bind to the template, but primer 5 will not. All the primers bound to the template will be extended with a fluorescein labeled dideoxy nucleotide, but those unbound will not. All primers will then be captured on microspheres and measured by flow cytometry as described above.

Example 3

Detection of Translocations by SBE

Figure 4:
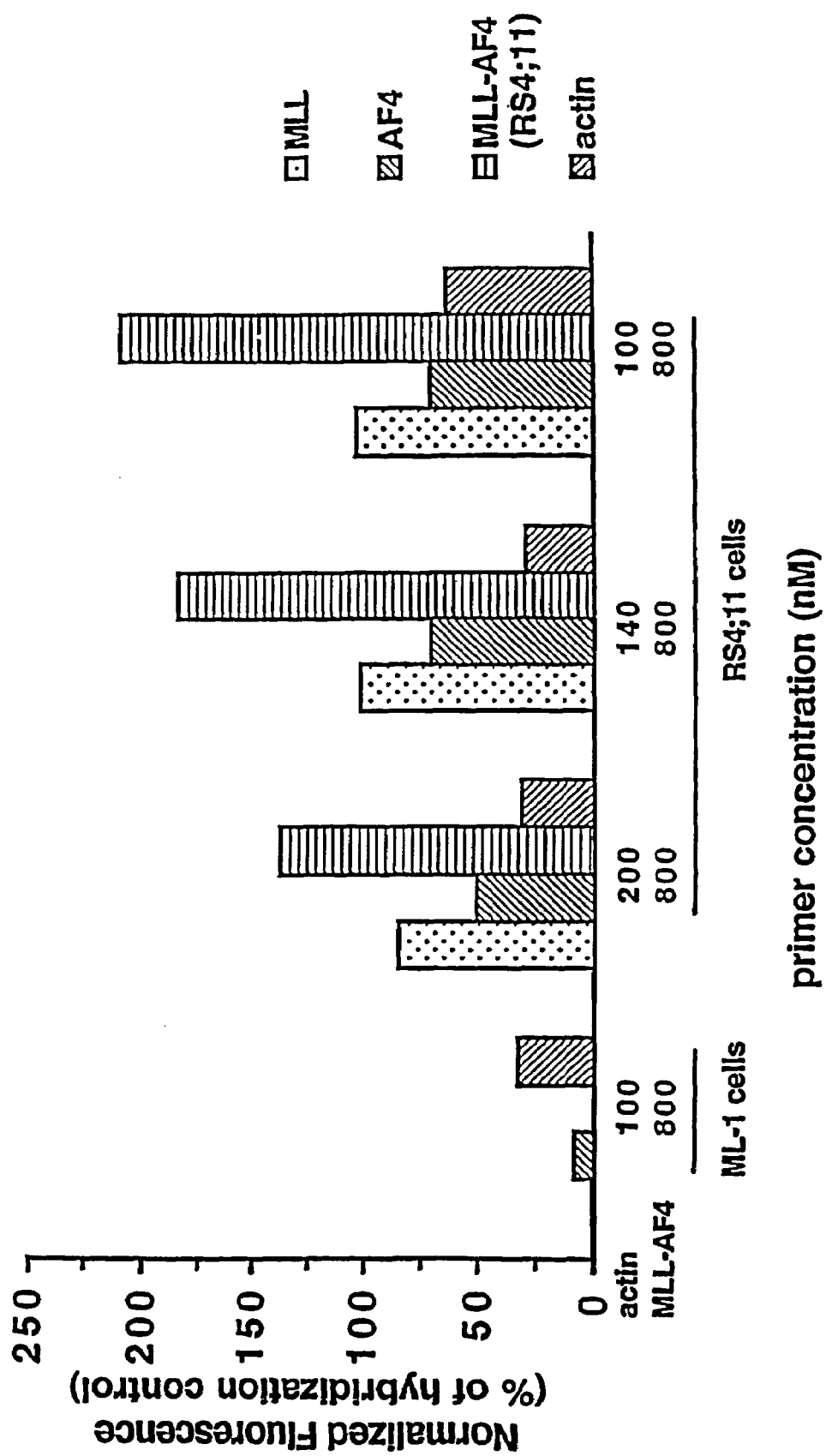
FIG. 4 demonstrates optimization of the primer ratio for duplex PCR. Ratios of 200 nM/800 nM, 140 nM/800 nM, and 100 nM/800 nM β-actin/MLL-AF4 fusion transcript primers were used. Different sizes microspheres were used. Specific fluorescence signals were normalized with the hybridization control signals generated by hybridizing the address tags on microspheres to capture tags.
Figure 5:
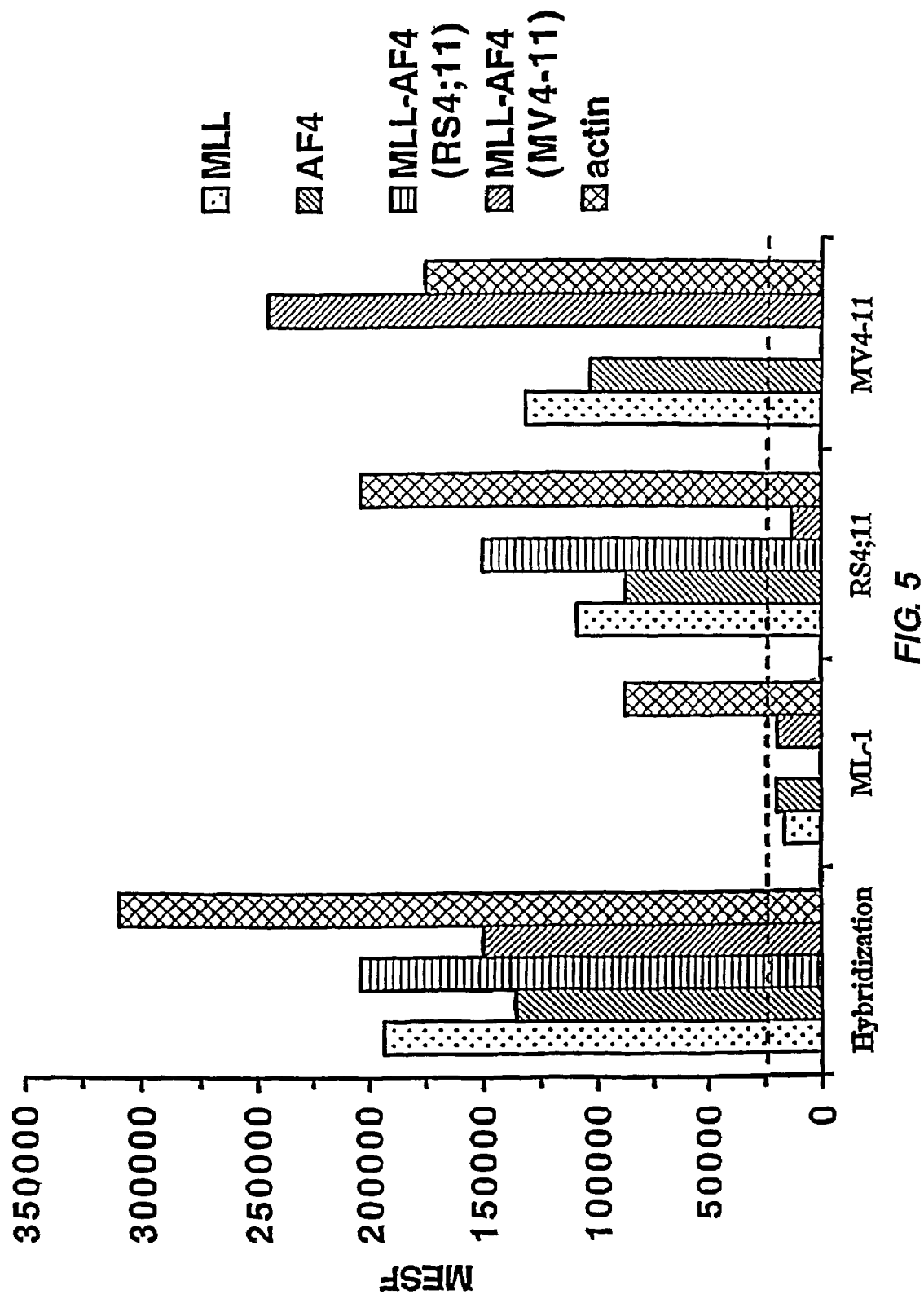
FIG. 5 demonstrates detection of the MLL-AF4 translocation in cells. Total RNA was isolated from human leukemia cells RS4;11, MV4-11, and ML-1 cells (control). RT-PCR and SBE were carried out as described in Example 1 below. Hybridization indicates the signals generated by hybridization of fluorescein labeled capture sequence tags with the corresponded address sequence tags on the microspheres. Nine pairs of SBE primers are employed for detection of nine translocations. Each pair of SBE primers targets one translocation. For example, MLL-A and AF4-B show the signals for the primers targeting the consensus sequence of all known transcripts of MLL-AF4 fusion genes. MLL-AF4 (RS4;11) shows that signals specific for the primer which targets the specific junction sequence of the MLL-AF4 transcript in RS4;11 cells (e10-e4). MLL-AF4 (MV4-11) shows that signals specific for the primer which targets the specific junction sequence of the MLL-AF4 transcript in MV4-11 cells (e9-e5). Actin represents the signal for β-actin primer.
Figure 6:
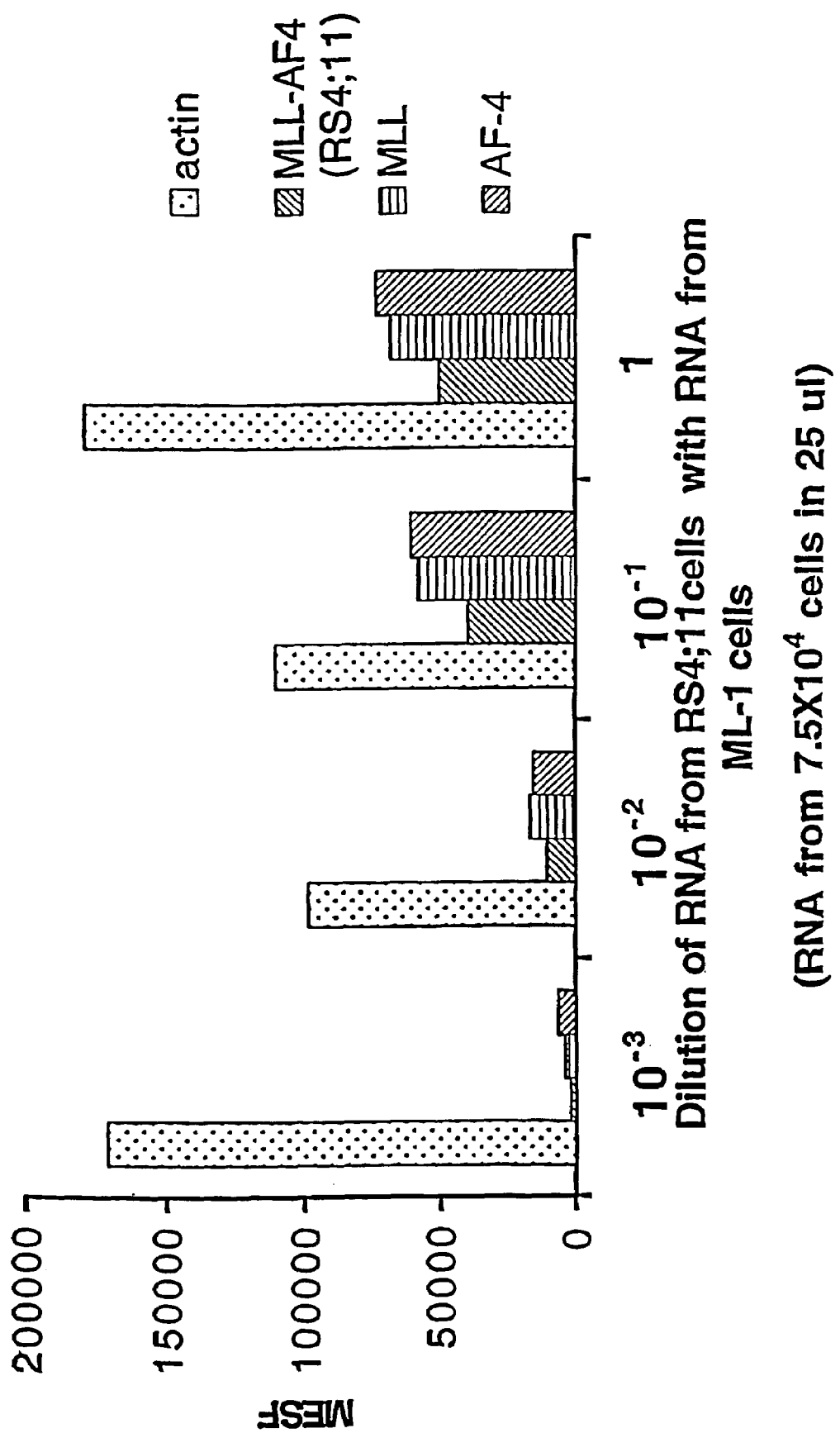
FIG. 6 demonstrates the detection sensitivity of SBE for MLL-AF4. Total RNA from approximately $7.5 \times 10^4$ RS4;11 cells was diluted 10 fold, 100, fold, and 1000 fold with RNA from ML-1 cells and SBE was performed. The dotted bar shows the signal for β-actin. The remaining bars show the signal for MLL-AF4 fusion transcripts.

A multiplex assay for detection of nine common and well-characterized translocations was designed. The schematic diagram for the nine translocations with the relative position of primers is shown in FIG. 17. One primer is designed for the sequence derived from one gene of each translocation, and the other primer is designed for the sequence derived from the other gene in the same translocation. The use of two consensus primers allows identification of the translocation no matter which transcription variant it is. The sequences for PCR primers and SBE primers are listed in Table 2 (FIG. 8) and Table 3 (FIG. 9) respectively. Data from one typical experiment is shown in FIG. 4. Hybridization indicated the fluorescence signals generated by hybridization of fluorescence labeled capture tags with complementary address tags immobilized on each color microspheres. In the control cells, only actin was detected. In the positive cell line, RS4;11, which has MLL-AF4 translocation, in addition to actin, MLL-AF4 translocation was detected by knowing the two SBE primers, MLL-A and AF4-B, were labeled with fluorescence dye. Primers for other translocations were not extended with fluorescence dye.

To verify the accuracy of the multiplex strategy, nine artificial DNA templates, each representing one translocation, and one β-actin DNA template were synthesized (FIG. 7 and Example 1). Experiment results for detection of these artificial translocations are shown in FIG. 11. For each DNA template, i.e., for each translocation, only one pair of corresponding SBE primers was extended with fluorescence dye. For example, for E2A-PEBX translocation, only SBE primers E2A-A and PBX-B were fluorescence extended, but not other SBE primers. In addition, the control primer, actin, was fluorescence extended for all samples.

To further validate this assay, nine translocation positive cell lines were employed. Both MV4-11 and RS4; 11 cell lines contain the MLL-AF4 translocation. The other six cell lines contain one unique translocation as indicated in FIG. 12. The translocation detected for each cell line matched the translocation previously reported for each cell line. β-actin was detected in all cell lines including control cell lines, HL-60 and ML-1.

Example 4

Identification of Multiple Fusion Transcripts by SBE

Once the translocation was detected, the transcription variants in the translocation were identified by similar approach. There are 10 known transcript variants of the MLL-AF4 translocation. FIG. 2 illustrates the ten known fusion transcripts for MLL-AF4 translocation. Two primers, MLL-A and AF4-B, target the consensus sequence derived from MLL and AF4 gene respectively. These two primers can be used to determine whether a MLL-AF4 translocation is present. A third primer for the specific junction sequence for each fusion transcript was also designed. The third primer can be used to identify the fusion transcript variant in the patient sample. For example, MLL-AF4-C targets the junction sequence of fusion transcript e8-e7, and will not bind to any other transcript variants; primer MLL-AF4-D will only bind to fusion transcript e8-e4. The sequences of all these SBE primers are listed in FIG. 13.

To verify the multiplex strategy, ten artificial DNA templates, each containing a unique junction sequence of one transcript variant of MLL-AF4 translocation, and one actin template for actin control were designed (FIG. 13 and Example 1). DNA MLL-AF4-CT targets MLL-AF4 fusion transcript (e8-e7); DNA MLL-AF4-DT targets MLL-AF4 fusion transcript (e8-e4) and so on. Data for detection of these fusion transcripts are shown in FIG. 15. Actin was detected in all DNA templates. The primers for consensus sequence, MLL and AF4, were extended with fluorescence dye. The specific primer complementary to the junction sequence of each DNA template, i.e., for each transcript variant, was only fluorescence labeled when the corresponding transcript variant was present. For example, in the presence of MLL-AF4-CT, MLL-A, AF4-B and actin, SBE primer MLL-AF4-C were extended with fluorescence dye, but the primers for other junction sequence were not.

In addition, two cell lines, MV4-11 and RS4;11, each containing the MLL-AF4 translocation but with different translocation junctions, were used to verify these results. In the control ML-1 cell line, only actin was detected. In both MLL-AF4 translocation-containing cell lines, the MLL-AF4 translocation and actin were detected. In addition, the specific primer against each translocation junction sequence was only extended with fluorescent nucleotides corresponding to complementary base of the translocation junction sequence. In another words, e9-e5 transcript variant was only detected in RS4;11 cell line but not in MV4-11 cell line, while e10-e4 transcript variant was only detected in MV4-11 cell line.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of detecting a chromosome translocation associated with leukemia, the method comprising:
    (a) amplifying a target nucleic acid sequence from a biological sample;
    (b) hybridizing a first oligonucleotide comprising the sequence set forth in SEQ ID NO: 40 to the amplified target under conditions in which the first oligonucleotide specifically hybridizes to a first region of the translocation,
    wherein the first oligonucleotide comprises a first capture tag;
    (c) hybridizing a second oligonucleotide comprising the sequence set forth in SEQ ID NO: 41 to the amplified target under conditions in which the second oligonucleotide specifically hybridizes to a second region of the translocation,
    wherein the second oligonucleotide comprises a second capture tag;

(d) extending the first and second hybridized oligonucleotide sequences to produce a first and a second labeled extended oligonucleotide;

(e) hybridizing the first and second oligonucleotides to a first and a second address tag on a solid support under conditions in which the first and second address tags specifically hybridize to the first and second capture tags; and (f) detecting the presence of the first and second labeled extended oligonucleotides on the solid support, thereby detecting the presence of the chromosome translocation associated with leukemia.

2. The method of claim 1, further comprising (g) hybridizing a third oligonucleotide comprising the sequence set forth in SEQ ID NO: 93 to the amplified target under conditions in which the third oligonucleotide specifically hybridizes to a junction region within the translocation, wherein the third oligonucleotide comprises a third capture tag;

(h) extending the third hybridized oligonucleotide sequence to produce a third labeled extended oligonucleotide;

(i) hybridizing the third oligonucleotide to a third address tag on a solid support under conditions in which the third address tag specifically hybridizes to the third capture tag; and (j) detecting the presence of the third labeled extended oligonucleotide on the solid support, thereby detecting the presence of the junction region.

3. A method for detecting cancer by detecting a chromosome translocation pattern associated with leukemia, the method comprising:

(a) amplifying a target nucleic acid from a biological sample;

(b) hybridizing a first oligonucleotide comprising the seciuence set forth in SEQ ID NO: 40 to the amplified target under conditions in which the first oligonucleotide specifically hybridizes to a first region of the translocation, wherein the first oligonucleotide comprises a first capture tag;

(c) hybridizing a second oligonucleotide comprising the sequence set forth in SEQ ID NO: 41 to the amplified target under conditions in which the second oligonucleotide specifically hybridizes to a second region of the translocation, wherein the second oligonucleotide comprises second a capture tag;

(d) hybridizing a third oligonucleotide comprising the sequence set forth in SEQ ID NO: 93 to the amplified target under conditions in which the third oligonucleotide specifically hybridizes to a junction region within the translocation, wherein the third oligonucleotide comprises a third capture tag;

(e) extending the first, second, and third hybridized oligonucleotide sequences to produce a first, second, and third labeled extended oligonucleotide;

(f) hybridizing the first, second, and third oligonucleotides to a first, a second, and a third address tag on a solid support under conditions in which the first, second, and third labeled extended oligonucleotides specifically hybridize to the first, second, and third address tag; and (g) detecting the presence of the first, second, and third labeled extended oligonucleotides on the solid support, thereby detecting the presence of the chromosome translocation pattern associated with leukemia.

4. The method of claim 3, wherein the third oligonucleotide comprises SEQ ID NO: 93.

5. A method of detecting a chromosome translocation associated with leukemia, the method comprising:

(a) amplifying a target nucleic acid sequence from a biological sample;

(b) hybridizing a first oligonucleotide comprising the sequence set forth in SEQ ID NO: 87 to the amplified target under conditions in which the first oligonucleotide specifically hybridizes to a first region of the translocation, wherein the first oligonucleotide comprises a first capture tag;

(c) hybridizing a second oligonucleotide comprising the sequence set forth in SEQ ID NO: 88 to the amplified target under conditions in which the second oligonucleotide specifically hybridizes to a second region of the translocation, wherein the second oligonucleotide comprises a second capture tag;

(d) extending the first and second hybridized oligonucleotide sequences to produce a first and a second labeled extended oligonucleotide;

(e) hybridizing the first and second oligonucleotides to a first and a second address tag on a solid support under conditions in which the first and second address tags specifically hybridize to the first and second capture tags;

(f) detecting the presence of the first and second labeled extended oligonucleotides on the solid support, thereby detecting the presence of the chromosome translocation associated with leukemia, (g) hybridizing a third oligonucleotide comprising the sequence set forth in SEQ ID NO: 93 to the amplified target under conditions in which the third oligonucleotide specifically hybridizes to a junction region within the translocation, wherein the third oligonucleotide comprises a third capture tag;

(h) extending the third hybridized oligonucleotide sequence to produce a third labeled extended oligonucleotide;

(i) hybridizing the third oligonucleotide to a third address tag on a solid support under conditions in which the third address tag specifically hybridizes to the third capture tag; and (j) detecting the presence of the third labeled extended oligonucleotide on the solid support, thereby detecting the presence of the junction region.

6. A method of detecting a chromosome translocation associated with leukemia, the method comprising:

(a) amplifying a target nucleic acid sequence from a biological sample;

(b) hybridizing a first oligonucleotide comprising the sequence set forth in SEQ ID NO :91 to the amplified target under conditions in which the first oligonucleotide specifically hybridizes to a first region of the translocation, wherein the first oligonucleotide comprises a first capture tag;

(c) hybridizing a second oligonucleotide comprising the sequence set forth in SEQ ID NO:92 to the amplified target under conditions in which the second oligonucleotide specifically hybridizes to a second region of the translocation, wherein the second oligonucleotide comprises a second capture tag;

(d) extending the first and second hybridized oligonucleotide sequences to produce a first and a second labeled extended oligonucleotide;

(e) hybridizing the first and second oligonucleotides to a first and a second address tag on a solid support under conditions in which the first and second address tags specifically hybridize to the first and second capture tags;

(f) detecting the presence of the first and second labeled extended oligonucleotides on the solid support, thereby detecting the presence of the chromosome translocation associated with leukemia, (g) hybridizing a third oligonucleotide comprising the sequence set forth in SEQ ID NO:93 to the amplified target under conditions in which the third oligonucleotide specifically hybridizes to a junction region within the translocation, wherein the third oligonucleotide comprises a third capture tag;

(h) extending the third hybridized oligonucleotide sequence to produce a third labeled extended oligonucleotide;

(i) hybridizing the third oligonucleotide to a third address tag on a solid support under conditions in which the third address tag specifically hybridizes to the third capture tag; and (j) detecting the presence of the third labeled extended oligonucleotide on the solid support, thereby detecting the presence of the junction region.

* * * * *

SEQUENCE LISTING

```
<160> NUMBER OF SEQ ID NOS: 103

<210> SEQ ID NO 1
<211> LENGTH: 45
<212> TYPE: DNA
<213> ORGANISM: Artificial Sequence
<220> FEATURE:
<223> OTHER INFORMATION: template oligo E2A-T

<400> SEQUENCE: 1
ccaggcaccc tccctgacct gtctcggcct cccgactcct acagt             45

<210> SEQ ID NO 2
<211> LENGTH: 45
<212> TYPE: DNA
<213> ORGANISM: Artificial Sequence
<220> FEATURE:
<223> OTHER INFORMATION: template oligo PBX1-T

<400> SEQUENCE: 2
ccagctgatg cggctggaca acatgctgtt agcggaaggc gtggc             45

<210> SEQ ID NO 3
<211> LENGTH: 45
<212> TYPE: DNA
<213> ORGANISM: Artificial Sequence
<220> FEATURE:
<223> OTHER INFORMATION: template oligo AF4-T

<400> SEQUENCE: 3
gatacatctt caaaaactca ctcaaattct cagcaaggaa cgtca             45

<210> SEQ ID NO 4
<211> LENGTH: 45
<212> TYPE: DNA
<213> ORGANISM: Artificial Sequence
<220> FEATURE:
<223> OTHER INFORMATION: template oligo MLL-T

<400> SEQUENCE: 4
aagaagttcc caaaccact cctagtgagc ccaagaaaaa gcagc              45

<210> SEQ ID NO 5
<211> LENGTH: 45
<212> TYPE: DNA
<213> ORGANISM: Artificial Sequence
<220> FEATURE:
<223> OTHER INFORMATION: template oligo AML1-T

<400> SEQUENCE: 5
aaagcttcac tctgaccatc actgtcttca caaacccacc gcaag             45

<210> SEQ ID NO 6
<211> LENGTH: 45
<212> TYPE: DNA
<213> ORGANISM: Artificial Sequence
<220> FEATURE:
```

<223> OTHER INFORMATION: template oligo ETO-T

<400> SEQUENCE: 6
ggatgtgaag acgcaatcta ggctgactcc tccaacaatg ccacc        45

<210> SEQ ID NO 7
<211> LENGTH: 45
<212> TYPE: DNA
<213> ORGANISM: Artificial Sequence
<220> FEATURE:
<223> OTHER INFORMATION: template oligo BCR1-T

<400> SEQUENCE: 7
ctcgcagaac tcgcaacagt ccttcgacag cagcagtccc cccac        45

<210> SEQ ID NO 8
<211> LENGTH: 45
<212> TYPE: DNA
<213> ORGANISM: Artificial Sequence
<220> FEATURE:
<223> OTHER INFORMATION: template oligo ABL-T

<400> SEQUENCE: 8
ctccgggtct taggctataa tcacaatggg gaatggtgtg aagcc        45

<210> SEQ ID NO 9
<211> LENGTH: 45
<212> TYPE: DNA
<213> ORGANISM: Artificial Sequence
<220> FEATURE:
<223> OTHER INFORMATION: template oligo BCR2-T

<400> SEQUENCE: 9
actccagact gtccacagca ttccgctgac catcaataag gaaga        45

<210> SEQ ID NO 10
<211> LENGTH: 45
<212> TYPE: DNA
<213> ORGANISM: Artificial Sequence
<220> FEATURE:
<223> OTHER INFORMATION: template oligo TEL-T

<400> SEQUENCE: 10
ctggcttaca tgaaccacat catggtctct gtctccccgc ctgaa        45

<210> SEQ ID NO 11
<211> LENGTH: 45
<212> TYPE: DNA
<213> ORGANISM: Artificial Sequence
<220> FEATURE:
<223> OTHER INFORMATION: template oligo AML1-B-T

<400> SEQUENCE: 11
ccattgggag aatagcagat gccagcacga gccgccgctt cacgc        45

<210> SEQ ID NO 12
<211> LENGTH: 45
<212> TYPE: DNA
<213> ORGANISM: Artificial Sequence
<220> FEATURE:
<223> OTHER INFORMATION: template oligo PML-T

<400> SEQUENCE: 12
gagttcaagg tgcgcctgca ggacctcagc tcttgcatca cccag        45

<210> SEQ ID NO 13
<211> LENGTH: 45
<212> TYPE: DNA
<213> ORGANISM: Artificial Sequence
<220> FEATURE:
<223> OTHER INFORMATION: template oligo RARA-T

<400> SEQUENCE: 13
ccagagcagc agttctgaag agatagtgcc cagccctccc tcgcc          45

<210> SEQ ID NO 14
<211> LENGTH: 45
<212> TYPE: DNA
<213> ORGANISM: Artificial Sequence
<220> FEATURE:
<223> OTHER INFORMATION: template oligo CBFB-T

<400> SEQUENCE: 14
gtatgggctg tctggagttt gatgaggagc gagcccagca ggagg          45

<210> SEQ ID NO 15
<211> LENGTH: 45
<212> TYPE: DNA
<213> ORGANISM: Artificial Sequence
<220> FEATURE:
<223> OTHER INFORMATION: template oligo MYH11-T

<400> SEQUENCE: 15
ggccctggag acccagatgg aggagatgaa gacgcagctg aaaga          45

<210> SEQ ID NO 16
<211> LENGTH: 45
<212> TYPE: DNA
<213> ORGANISM: Artificial Sequence
<220> FEATURE:
<223> OTHER INFORMATION: template oligo SIL-T

<400> SEQUENCE: 16
ctcccgctcc taccctgcaa acagacctca gctccgcgga agttg          45

<210> SEQ ID NO 17
<211> LENGTH: 45
<212> TYPE: DNA
<213> ORGANISM: Artificial Sequence
<220> FEATURE:
<223> OTHER INFORMATION: template oligo TAL-T

<400> SEQUENCE: 17
gccgagcgag gcggctcgca gtgacccca gctagaggga cggga           45

<210> SEQ ID NO 18
<211> LENGTH: 45
<212> TYPE: DNA
<213> ORGANISM: Artificial Sequence
<220> FEATURE:
<223> OTHER INFORMATION: template oligo Actin-T

<400> SEQUENCE: 18
cacccagcac aatgaagatc aagatcattg ctcctcctga gcgca          45

<210> SEQ ID NO 19
<211> LENGTH: 19
<212> TYPE: DNA
<213> ORGANISM: Artificial Sequence
<220> FEATURE:
<223> OTHER INFORMATION: PCR primer E2A-F

```
<400> SEQUENCE: 19
caccagcctc atgcacaac                                                  19

<210> SEQ ID NO 20
<211> LENGTH: 19
<212> TYPE: DNA
<213> ORGANISM: Artificial Sequence
<220> FEATURE:
<223> OTHER INFORMATION: PCR primer PBX-R

<400> SEQUENCE: 20
tcgcaggaga ttcatcacg                                                  19

<210> SEQ ID NO 21
<211> LENGTH: 17
<212> TYPE: DNA
<213> ORGANISM: Artificial Sequence
<220> FEATURE:
<223> OTHER INFORMATION: PCR primer MLL-F

<400> SEQUENCE: 21
ccgcctcagc cacctac                                                    17

<210> SEQ ID NO 22
<211> LENGTH: 20
<212> TYPE: DNA
<213> ORGANISM: Artificial Sequence
<220> FEATURE:
<223> OTHER INFORMATION: PCR primer AF4-R

<400> SEQUENCE: 22
tgtcactgag ctgaaggtcg                                                 20

<210> SEQ ID NO 23
<211> LENGTH: 21
<212> TYPE: DNA
<213> ORGANISM: Artificial Sequence
<220> FEATURE:
<223> OTHER INFORMATION: PCR primer AML1-A-F

<400> SEQUENCE: 23
ctaccgcagc catgaagaac c                                               21

<210> SEQ ID NO 24
<211> LENGTH: 21
<212> TYPE: DNA
<213> ORGANISM: Artificial Sequence
<220> FEATURE:
<223> OTHER INFORMATION: PCR primer ETO-R

<400> SEQUENCE: 24
agaggaaggc ccattgctga a                                               21

<210> SEQ ID NO 25
<211> LENGTH: 21
<212> TYPE: DNA
<213> ORGANISM: Artificial Sequence
<220> FEATURE:
<223> OTHER INFORMATION: PCR primer BCR1-F

<400> SEQUENCE: 25
gactgcagct ccaatgagaa c                                               21

<210> SEQ ID NO 26
<211> LENGTH: 21
```

<212> TYPE: DNA
<213> ORGANISM: Artificial Sequence
<220> FEATURE:
<223> OTHER INFORMATION: PCR primer ABL-R

<400> SEQUENCE: 26
gtttgggctt cacaccattc c                                          21

<210> SEQ ID NO 27
<211> LENGTH: 22
<212> TYPE: DNA
<213> ORGANISM: Artificial Sequence
<220> FEATURE:
<223> OTHER INFORMATION: PCR primer BCR2-F

<400> SEQUENCE: 27
gaagtgtttc agaagcttct cc                                         22

<210> SEQ ID NO 28
<211> LENGTH: 20
<212> TYPE: DNA
<213> ORGANISM: Artificial Sequence
<220> FEATURE:
<223> OTHER INFORMATION: PCR primer TEL-F

<400> SEQUENCE: 28
tgcaccctct gatcctgaac                                            20

<210> SEQ ID NO 29
<211> LENGTH: 19
<212> TYPE: DNA
<213> ORGANISM: Artificial Sequence
<220> FEATURE:
<223> OTHER INFORMATION: PCR primer AML1-B-R

<400> SEQUENCE: 29
aacgcctcgc tcatcttgc                                             19

<210> SEQ ID NO 30
<211> LENGTH: 18
<212> TYPE: DNA
<213> ORGANISM: Artificial Sequence
<220> FEATURE:
<223> OTHER INFORMATION: PCR primer PML-F

<400> SEQUENCE: 30
ctgctggagg ctgtggac                                              18

<210> SEQ ID NO 31
<211> LENGTH: 20
<212> TYPE: DNA
<213> ORGANISM: Artificial Sequence
<220> FEATURE:
<223> OTHER INFORMATION: PCR primer RARA-R

<400> SEQUENCE: 31
gcttgtagat gcggggtaga                                            20

<210> SEQ ID NO 32
<211> LENGTH: 22
<212> TYPE: DNA
<213> ORGANISM: Artificial Sequence
<220> FEATURE:
<223> OTHER INFORMATION: PCR primer CBFB-F

<400> SEQUENCE: 32

-continued

```
gcaggcaagg tatatttgaa gg                                              22

<210> SEQ ID NO 33
<211> LENGTH: 22
<212> TYPE: DNA
<213> ORGANISM: Artificial Sequence
<220> FEATURE:
<223> OTHER INFORMATION: PCR primer MYH11-R

<400> SEQUENCE: 33
tcctcttctc ctcattctgc tc                                              22

<210> SEQ ID NO 34
<211> LENGTH: 19
<212> TYPE: DNA
<213> ORGANISM: Artificial Sequence
<220> FEATURE:
<223> OTHER INFORMATION: PCR primer SIL-F

<400> SEQUENCE: 34
tcccgctcct accctgcaa                                                  19

<210> SEQ ID NO 35
<211> LENGTH: 18
<212> TYPE: DNA
<213> ORGANISM: Artificial Sequence
<220> FEATURE:
<223> OTHER INFORMATION: PCR primer TAL1-R

<400> SEQUENCE: 35
cgcgcccagt tcgatgac                                                   18

<210> SEQ ID NO 36
<211> LENGTH: 23
<212> TYPE: DNA
<213> ORGANISM: Artificial Sequence
<220> FEATURE:
<223> OTHER INFORMATION: PCR primer Actin-F

<400> SEQUENCE: 36
gccctggact tcgagcaaga gat                                             23

<210> SEQ ID NO 37
<211> LENGTH: 23
<212> TYPE: DNA
<213> ORGANISM: Artificial Sequence
<220> FEATURE:
<223> OTHER INFORMATION: PCR primer Actin-R

<400> SEQUENCE: 37
cctcggccac attgtgaact ttg                                             23

<210> SEQ ID NO 38
<211> LENGTH: 40
<212> TYPE: DNA
<213> ORGANISM: Artificial Sequence
<220> FEATURE:
<223> OTHER INFORMATION: SBE primer E2A-A with capture tag

<400> SEQUENCE: 38
cgagagttag ctacaaagcc gacaggtcag ggagggtgcc                           40

<210> SEQ ID NO 39
<211> LENGTH: 43
<212> TYPE: DNA
<213> ORGANISM: Artificial Sequence
```

```
<220> FEATURE:
<223> OTHER INFORMATION: SBA primer PBX1-B with capture tag

<400> SEQUENCE: 39
cagaacgcat tgtgaatagg tgccttccgc taacagcatg ttg            43

<210> SEQ ID NO 40
<211> LENGTH: 44
<212> TYPE: DNA
<213> ORGANISM: Artificial Sequence
<220> FEATURE:
<223> OTHER INFORMATION: SBE primer MLL-A with capture tag

<400> SEQUENCE: 40
cacggatggg atatatgagc gcttttctt gggctcacta ggag            44

<210> SEQ ID NO 41
<211> LENGTH: 42
<212> TYPE: DNA
<213> ORGANISM: Artificial Sequence
<220> FEATURE:
<223> OTHER INFORMATION: SBE primer AF4-B with capture tag

<400> SEQUENCE: 41
gcacctagat aggatcgtac ctcgagcatg gatgacgttc ct             42

<210> SEQ ID NO 42
<211> LENGTH: 43
<212> TYPE: DNA
<213> ORGANISM: Artificial Sequence
<220> FEATURE:
<223> OTHER INFORMATION: SBE primer AML1-A with capture tag

<400> SEQUENCE: 42
gtccaagcta gagcgttacg tgggtttgtg aagacagtga tgg            43

<210> SEQ ID NO 43
<211> LENGTH: 46
<212> TYPE: DNA
<213> ORGANISM: Artificial Sequence
<220> FEATURE:
<223> OTHER INFORMATION: SBE primer ETO-B with capture tag

<400> SEQUENCE: 43
gaattggggc tacgaataat gtcattgttg gaggagtcag cctaga         46

<210> SEQ ID NO 44
<211> LENGTH: 41
<212> TYPE: DNA
<213> ORGANISM: Artificial Sequence
<220> FEATURE:
<223> OTHER INFORMATION: SBE primer BCR1-A with capture tag

<400> SEQUENCE: 44
tcgtccggta aagataatcg ggactgctgc tgtcgaagga c              41

<210> SEQ ID NO 45
<211> LENGTH: 42
<212> TYPE: DNA
<213> ORGANISM: Artificial Sequence
<220> FEATURE:
<223> OTHER INFORMATION: SBE primer ABL-B with capture tag

<400> SEQUENCE: 45
tctgtaggag ggcaagaaac acaccattcc ccattgtgat ta             42
```

-continued

<210> SEQ ID NO 46
<211> LENGTH: 41
<212> TYPE: DNA
<213> ORGANISM: Artificial Sequence
<220> FEATURE:
<223> OTHER INFORMATION: SBE primer BCR2-A with capture tag

<400> SEQUENCE: 46
cctccgccat tacctaact tattgatggt cagcggaatg c        41

<210> SEQ ID NO 47
<211> LENGTH: 42
<212> TYPE: DNA
<213> ORGANISM: Artificial Sequence
<220> FEATURE:
<223> OTHER INFORMATION: SBE primer TEL-A with capture tag

<400> SEQUENCE: 47
tgtcgctaat tagttggctg cggggagaca gagaccatga tg       42

<210> SEQ ID NO 48
<211> LENGTH: 42
<212> TYPE: DNA
<213> ORGANISM: Artificial Sequence
<220> FEATURE:
<223> OTHER INFORMATION: SBE primer AML1-B with capture tag

<400> SEQUENCE: 48
cagactgaga tacttcacta cgcagcacgg agcagaggaa gt       42

<210> SEQ ID NO 49
<211> LENGTH: 43
<212> TYPE: DNA
<213> ORGANISM: Artificial Sequence
<220> FEATURE:
<223> OTHER INFORMATION: SBE primer PML-A with capture tag

<400> SEQUENCE: 49
gcggctctat ttgaattttc gggtgatgca agagctgagg tcc      43

<210> SEQ ID NO 50
<211> LENGTH: 41
<212> TYPE: DNA
<213> ORGANISM: Artificial Sequence
<220> FEATURE:
<223> OTHER INFORMATION: SBE primer RARA-B with capture tag

<400> SEQUENCE: 50
cctccttcct tcataagcgt gggagggctg ggcactatct c        41

<210> SEQ ID NO 51
<211> LENGTH: 39
<212> TYPE: DNA
<213> ORGANISM: Artificial Sequence
<220> FEATURE:
<223> OTHER INFORMATION: SBE primer CBFB-A with capture tag

<400> SEQUENCE: 51
tgactcgact tttgggagtg ggctcgctcc tcatcaaac          39

<210> SEQ ID NO 52
<211> LENGTH: 43
<212> TYPE: DNA
<213> ORGANISM: Artificial Sequence
<220> FEATURE:
<223> OTHER INFORMATION: SBE primer MYH11-B with capture tag

```
<400> SEQUENCE: 52
aattcggacc ctaacatctc gctgcgtctt catctcctcc atc                    43

<210> SEQ ID NO 53
<211> LENGTH: 40
<212> TYPE: DNA
<213> ORGANISM: Artificial Sequence
<220> FEATURE:
<223> OTHER INFORMATION: SBE primer SIL-A with capture tag

<400> SEQUENCE: 53
cgacagccga taaacgagga gctgaggtct gtttgcaggg                        40

<210> SEQ ID NO 54
<211> LENGTH: 39
<212> TYPE: DNA
<213> ORGANISM: Artificial Sequence
<220> FEATURE:
<223> OTHER INFORMATION: SBE primer TAL1-B with capture tag

<400> SEQUENCE: 54
ggtctcttga tcaggacggt ccctctagct gggggtcac                         39

<210> SEQ ID NO 55
<211> LENGTH: 44
<212> TYPE: DNA
<213> ORGANISM: Artificial Sequence
<220> FEATURE:
<223> OTHER INFORMATION: SBE primer Actin with capture tag

<400> SEQUENCE: 55
ggtatagcca tgcgaggtgt caggaggagc aatgatcttg atct                   44

<210> SEQ ID NO 56
<211> LENGTH: 20
<212> TYPE: DNA
<213> ORGANISM: Artificial Sequence
<220> FEATURE:
<223> OTHER INFORMATION: SBE primer E2A-A

<400> SEQUENCE: 56
gacaggtcag ggagggtgcc                                              20

<210> SEQ ID NO 57
<211> LENGTH: 22
<212> TYPE: DNA
<213> ORGANISM: Artificial Sequence
<220> FEATURE:
<223> OTHER INFORMATION: SBE primer PBX1-B

<400> SEQUENCE: 57
gccttccgct aacagcatgt tg                                           22

<210> SEQ ID NO 58
<211> LENGTH: 24
<212> TYPE: DNA
<213> ORGANISM: Artificial Sequence
<220> FEATURE:
<223> OTHER INFORMATION: SBE primer MLL-A

<400> SEQUENCE: 58 gcttttctt gggctcacta ggag                                          24

<210> SEQ ID NO 59
```

-continued

```
<211> LENGTH: 21
<212> TYPE: DNA
<213> ORGANISM: Artificial Sequence
<220> FEATURE:
<223> OTHER INFORMATION: SBE primer AF4-B

<400> SEQUENCE: 59
tcgagcatgg atgacgttcc t                                          21

<210> SEQ ID NO 60
<211> LENGTH: 21
<212> TYPE: DNA
<213> ORGANISM: Artificial Sequence
<220> FEATURE:
<223> OTHER INFORMATION: SBE primer AML1-A

<400> SEQUENCE: 60
ggtttgtgaa gacagtgatg g                                          21

<210> SEQ ID NO 61
<211> LENGTH: 24
<212> TYPE: DNA
<213> ORGANISM: Artificial Sequence
<220> FEATURE:
<223> OTHER INFORMATION: SBE primer ETO-B

<400> SEQUENCE: 61
cattgttgga ggagtcagcc taga                                       24

<210> SEQ ID NO 62
<211> LENGTH: 21
<212> TYPE: DNA
<213> ORGANISM: Artificial Sequence
<220> FEATURE:
<223> OTHER INFORMATION: SBE primer BCR1-A

<400> SEQUENCE: 62
ggactgctgc tgtcgaagga c                                          21

<210> SEQ ID NO 63
<211> LENGTH: 23
<212> TYPE: DNA
<213> ORGANISM: Artificial Sequence
<220> FEATURE:
<223> OTHER INFORMATION: SBE primer ABL-B

<400> SEQUENCE: 63
cacaccattc cccattgtga tta                                        23

<210> SEQ ID NO 64
<211> LENGTH: 22
<212> TYPE: DNA
<213> ORGANISM: Artificial Sequence
<220> FEATURE:
<223> OTHER INFORMATION: SBE primer BCR2-A

<400> SEQUENCE: 64
ttattgatgg tcagcggaat gc                                         22

<210> SEQ ID NO 65
<211> LENGTH: 22
<212> TYPE: DNA
<213> ORGANISM: Artificial Sequence
<220> FEATURE:
<223> OTHER INFORMATION: SBE primer TEL-A

<400> SEQUENCE: 65
```
cggggagaca gagaccatga tg       22

<210> SEQ ID NO 66
<211> LENGTH: 20
<212> TYPE: DNA
<213> ORGANISM: Artificial Sequence
<220> FEATURE:
<223> OTHER INFORMATION: SBE primer AML1-B

<400> SEQUENCE: 66
cagcacggag cagaggaagt          20

<210> SEQ ID NO 67
<211> LENGTH: 22
<212> TYPE: DNA
<213> ORGANISM: Artificial Sequence
<220> FEATURE:
<223> OTHER INFORMATION: SBE primer PML-A

<400> SEQUENCE: 67
ggtgatgcaa gagctgaggt cc       22

<210> SEQ ID NO 68
<211> LENGTH: 21
<212> TYPE: DNA
<213> ORGANISM: Artificial Sequence
<220> FEATURE:
<223> OTHER INFORMATION: SBE primer RARA-B

<400> SEQUENCE: 68
gggagggctg ggcactatct c        21

<210> SEQ ID NO 69
<211> LENGTH: 21
<212> TYPE: DNA
<213> ORGANISM: Artificial Sequence
<220> FEATURE:
<223> OTHER INFORMATION: SBA primer CBFB-A

<400> SEQUENCE: 69
tgggctcgct cctcatcaaa c        21

<210> SEQ ID NO 70
<211> LENGTH: 23
<212> TYPE: DNA
<213> ORGANISM: Artificial Sequence
<220> FEATURE:
<223> OTHER INFORMATION: SBA primer MYH11-B

<400> SEQUENCE: 70
gctgcgtctt catctcctcc atc      23

<210> SEQ ID NO 71
<211> LENGTH: 22
<212> TYPE: DNA
<213> ORGANISM: Artificial Sequence
<220> FEATURE:
<223> OTHER INFORMATION: SBE primer SIL-A

<400> SEQUENCE: 71
gagctgaggt ctgtttgcag gg       22

<210> SEQ ID NO 72
<211> LENGTH: 21
<212> TYPE: DNA

```
<213> ORGANISM: Artificial Sequence
<220> FEATURE:
<223> OTHER INFORMATION: SBE primer TAL1-B

<400> SEQUENCE: 72
gtccctctag ctgggggtca c                                      21

<210> SEQ ID NO 73
<211> LENGTH: 25
<212> TYPE: DNA
<213> ORGANISM: Artificial Sequence
<220> FEATURE:
<223> OTHER INFORMATION: SBE primer Actin

<400> SEQUENCE: 73
tcaggaggag caatgatctt gatct                                  25

<210> SEQ ID NO 74
<211> LENGTH: 45
<212> TYPE: DNA
<213> ORGANISM: Artificial Sequence
<220> FEATURE:
<223> OTHER INFORMATION: template oligo MLL-T

<400> SEQUENCE: 74
agaaaagaag ttcccaaaac cactcctagt gagcccaaga aaaag            45

<210> SEQ ID NO 75
<211> LENGTH: 45
<212> TYPE: DNA
<213> ORGANISM: Artificial Sequence
<220> FEATURE:
<223> OTHER INFORMATION: template oligo AF4-T

<400> SEQUENCE: 75
ccaaaaacaa tatgatacat cttcaaaaac tcactcaaat tctca            45

<210> SEQ ID NO 76
<211> LENGTH: 45
<212> TYPE: DNA
<213> ORGANISM: Artificial Sequence
<220> FEATURE:
<223> OTHER INFORMATION: template oligo MLL-AF4-CT

<400> SEQUENCE: 76
tccaccacca gaatcagaac aatatgatac atcttcaaaa actca            45

<210> SEQ ID NO 77
<211> LENGTH: 45
<212> TYPE: DNA
<213> ORGANISM: Artificial Sequence
<220> FEATURE:
<223> OTHER INFORMATION: template oligo MLL-AF4-DT

<400> SEQUENCE: 77
agcagcctcc accaccagaa tcagcagacc tactccaatg aagtc            45

<210> SEQ ID NO 78
<211> LENGTH: 45
<212> TYPE: DNA
<213> ORGANISM: Artificial Sequence
<220> FEATURE:
<223> OTHER INFORMATION: template oligo MLL-AF4-ET

<400> SEQUENCE: 78
gtaaaacaaa aaccaaaaga aaaggaaatg acccattcat ggccg            45
```

<210> SEQ ID NO 79
<211> LENGTH: 45
<212> TYPE: DNA
<213> ORGANISM: Artificial Sequence
<220> FEATURE:
<223> OTHER INFORMATION: template oligo MLL-AF4-FT

<400> SEQUENCE: 79
taaaacaaaa accaaaagaa aagcagacct actccaatga agtcc            45

<210> SEQ ID NO 80
<211> LENGTH: 45
<212> TYPE: DNA
<213> ORGANISM: Artificial Sequence
<220> FEATURE:
<223> OTHER INFORMATION: template oligo MLL-AF4-GT

<400> SEQUENCE: 80
cacaggatca gagtggactt taaggactct cagcatgtca gttct            45

<210> SEQ ID NO 81
<211> LENGTH: 45
<212> TYPE: DNA
<213> ORGANISM: Artificial Sequence
<220> FEATURE:
<223> OTHER INFORMATION: template oligo MLL-AF4-HT

<400> SEQUENCE: 81
cacaggatca gagtggactt taaggaaatg acccattcat ggccg            45

<210> SEQ ID NO 82
<211> LENGTH: 45
<212> TYPE: DNA
<213> ORGANISM: Artificial Sequence
<220> FEATURE:
<223> OTHER INFORMATION: template oligo MLL-AF4-IT

<400> SEQUENCE: 82
ccacaggatc agagtggact ttaagcagac ctactccaat gaagt            45

<210> SEQ ID NO 83
<211> LENGTH: 45
<212> TYPE: DNA
<213> ORGANISM: Artificial Sequence
<220> FEATURE:
<223> OTHER INFORMATION: template oligo MLL-AF4-JT

<400> SEQUENCE: 83
gccagtagtg ggcatgtaga ggactctcag catgtcagtt ctgta            45

<210> SEQ ID NO 84
<211> LENGTH: 45
<212> TYPE: DNA
<213> ORGANISM: Artificial Sequence
<220> FEATURE:
<223> OTHER INFORMATION: template oligo MLL-AF4-KT

<400> SEQUENCE: 84
tctgtgccag tagtgggcat gtagaggaaa tgacccattc atggc            45

<210> SEQ ID NO 85
<211> LENGTH: 45
<212> TYPE: DNA
<213> ORGANISM: Artificial Sequence
<220> FEATURE:

<223> OTHER INFORMATION: template oligo MLL-AF4-LT

<400> SEQUENCE: 85
tctgtgccag tagtgggcat gtagagcaga cctactccaa tgaag        45

<210> SEQ ID NO 86
<211> LENGTH: 45
<212> TYPE: DNA
<213> ORGANISM: Artificial Sequence
<220> FEATURE:
<223> OTHER INFORMATION: template oligo Actin-T

<400> SEQUENCE: 86
tggcacccag cacaatgaag atcaagatca ttgctcctcc tgagc        45

<210> SEQ ID NO 87
<211> LENGTH: 17
<212> TYPE: DNA
<213> ORGANISM: Artificial Sequence
<220> FEATURE:
<223> OTHER INFORMATION: PCR primer MLL-F

<400> SEQUENCE: 87
ccgcctcagc cacctac        17

<210> SEQ ID NO 88
<211> LENGTH: 20
<212> TYPE: DNA
<213> ORGANISM: Artificial Sequence
<220> FEATURE:
<223> OTHER INFORMATION: PCR primer AF4-R

<400> SEQUENCE: 88
tgtcactgag ctgaaggtcg        20

<210> SEQ ID NO 89
<211> LENGTH: 23
<212> TYPE: DNA
<213> ORGANISM: Artificial Sequence
<220> FEATURE:
<223> OTHER INFORMATION: PCR primer Actin-F

<400> SEQUENCE: 89
gccctggact tcgagcaaga gat        23

<210> SEQ ID NO 90
<211> LENGTH: 23
<212> TYPE: DNA
<213> ORGANISM: Artificial Sequence
<220> FEATURE:
<223> OTHER INFORMATION: PCR primer Actin-R

<400> SEQUENCE: 90
cctcggccac attgtgaact ttg        23

<210> SEQ ID NO 91
<211> LENGTH: 40
<212> TYPE: DNA
<213> ORGANISM: Artificial Sequence
<220> FEATURE:
<223> OTHER INFORMATION: SBE primer MLL-A

<400> SEQUENCE: 91
tctcatggcg aaaccggaac tttcttgggc tcactaggag        40

```
<210> SEQ ID NO 92
<211> LENGTH: 44
<212> TYPE: DNA
<213> ORGANISM: Artificial Sequence
<220> FEATURE:
<223> OTHER INFORMATION: SBE primer AF4-B

<400> SEQUENCE: 92
atatttggcg ggaaacacgt aatttgagtg agtttttgaa gatg                    44

<210> SEQ ID NO 93
<211> LENGTH: 42
<212> TYPE: DNA
<213> ORGANISM: Artificial Sequence
<220> FEATURE:
<223> OTHER INFORMATION: SBE primer MLL-AF4-C

<400> SEQUENCE: 93
tggtgagata cccgggttca catgaatggg tcatttcctt tt                      42

<210> SEQ ID NO 94
<211> LENGTH: 44
<212> TYPE: DNA
<213> ORGANISM: Artificial Sequence
<220> FEATURE:
<223> OTHER INFORMATION: SBE primer MLL-AF4-D

<400> SEQUENCE: 94
gtccgtccct taaggtggtt tcattggagt aggtctgctt aaag                    44

<210> SEQ ID NO 95
<211> LENGTH: 43
<212> TYPE: DNA
<213> ORGANISM: Artificial Sequence
<220> FEATURE:
<223> OTHER INFORMATION: SBE primer MLL-AF4-E

<400> SEQUENCE: 95
ttgggtcctt ccgagggtac atgaatgggt catttcctct aca                     43

<210> SEQ ID NO 96
<211> LENGTH: 43
<212> TYPE: DNA
<213> ORGANISM: Artificial Sequence
<220> FEATURE:
<223> OTHER INFORMATION: SBE primer MLL-AF4-F

<400> SEQUENCE: 96
ctaccaagtc gccgaacaca cattggagta ggtctgctga ttc                     43

<210> SEQ ID NO 97
<211> LENGTH: 44
<212> TYPE: DNA
<213> ORGANISM: Artificial Sequence
<220> FEATURE:
<223> OTHER INFORMATION: SBE primer MLL-AF4-G

<400> SEQUENCE: 97
aacatcccgg cccagcaggt ctgacatgct gagagtcctc taca                    44

<210> SEQ ID NO 98
<211> LENGTH: 44
<212> TYPE: DNA
<213> ORGANISM: Artificial Sequence
<220> FEATURE:
<223> OTHER INFORMATION: SBE primer MLL-AF4-H
```

-continued

```
<400> SEQUENCE: 98
caatgccgtg gaacctgaaa tcattggagt aggtctgctc taca                    44

<210> SEQ ID NO 99
<211> LENGTH: 46
<212> TYPE: DNA
<213> ORGANISM: Artificial Sequence
<220> FEATURE:
<223> OTHER INFORMATION: SBE primer MLL-AF4-I

<400> SEQUENCE: 99
cgtagacagc aaggccattt tttgaagatg tatcatattg ttctga                  46

<210> SEQ ID NO 100
<211> LENGTH: 44
<212> TYPE: DNA
<213> ORGANISM: Artificial Sequence
<220> FEATURE:
<223> OTHER INFORMATION: SBE primer MLL-AF4-J

<400> SEQUENCE: 100
aagatggcgc gcaccctaat tcattggagt aggtctgctt ttct                    44

<210> SEQ ID NO 101
<211> LENGTH: 44
<212> TYPE: DNA
<213> ORGANISM: Artificial Sequence
<220> FEATURE:
<223> OTHER INFORMATION: SBE primer MLL-AF4-K

<400> SEQUENCE: 101
taaattggcc aaatgcttcg ctgacatgct gagagtcctt aaag                    44

<210> SEQ ID NO 102
<211> LENGTH: 43
<212> TYPE: DNA
<213> ORGANISM: Artificial Sequence
<220> FEATURE:
<223> OTHER INFORMATION: SBE primer MLL-AF4-L

<400> SEQUENCE: 102
cctatccttt gggcgaactg atgaatgggt catttcctta aag                     43

<210> SEQ ID NO 103
<211> LENGTH: 43
<212> TYPE: DNA
<213> ORGANISM: Artificial Sequence
<220> FEATURE:
<223> OTHER INFORMATION: SBE primer actin

<400> SEQUENCE: 103
ttagaacgcc tttagcagcc aggaggagca atgatcttga tct                     43
```